United States Patent
Huang et al.

(10) Patent No.: US 7,179,926 B2
(45) Date of Patent: Feb. 20, 2007

(54) ARYLOXYALKYLAMINE NK-1/SSRI INHIBITORS

(75) Inventors: Yazhong Huang, Branford, CT (US); Shuanghua Hu, Milford, CT (US); Andrew P. Degnan, New Haven, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 11/188,581

(22) Filed: Jul. 25, 2005

(65) Prior Publication Data

US 2006/0020019 A1 Jan. 26, 2006

Related U.S. Application Data

(60) Provisional application No. 60/591,037, filed on Jul. 26, 2004.

(51) Int. Cl.
C07D 333/16 (2006.01)
C07D 333/46 (2006.01)
C07C 211/00 (2006.01)
C07C 217/44 (2006.01)
C07C 321/06 (2006.01)
A61K 31/135 (2006.01)
A61K 31/38 (2006.01)

(52) U.S. Cl. .................. 549/75; 564/340; 564/346; 564/367; 514/438; 514/649; 514/651; 514/654

(58) Field of Classification Search .............. None
See application file for complete search history.

(56) References Cited

U.S. PATENT DOCUMENTS 6,136,824 A 10/2000 MacLeod et al.

6,441,237 B1 8/2002 Stransky et al.

FOREIGN PATENT DOCUMENTS

WO WO 2004/005255 A1 1/2004
WO WO 2004/005256 A2 1/2004

OTHER PUBLICATIONS

Database CAPLUS on STN, Acc. No. 2000:592689, Stransky et al., WO 2000048987 A1 (Aug. 24, 2000) (abstract).*
T. Ryckmans, et al, "First Dual $NK_1$, Antagonists-Serotonin Reuptake Inhibitors: Synthesis and SAR of a New Class of Potential Antidepressants," Bioorganic & Medicinal Chemistry Letters, 12, pp. 261-264, 2002.
R. M. Shafik, et al, "Synthesis and Biochemical Evaluation of 2-Arylpropane-1,3-Diamines: Potential Bilateral Diamino Dopaminergic Analogs," Alexandria Journal of Pharmaceutical Sciences, 2(2), pp. 155-160, 1988—Database CAPLUS on STN, Acc. No. 1989:614161.

* cited by examiner

*Primary Examiner*—Brian Davis
(74) *Attorney, Agent, or Firm*—James Epperson

(57) ABSTRACT

The invention encompasses compounds of Formula I, including pharmaceutically acceptable salts and solvates, their pharmaceutical compositions, and their use in treating disorders associated with an excess or imbalance of tachykinins or serotonin or both.

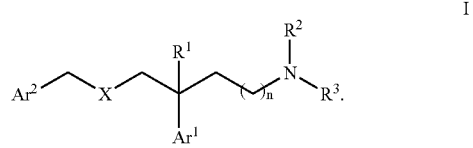

13 Claims, No Drawings

ARYLOXYALKYLAMINE NK-1/SSRI INHIBITORS

CROSS REFERENCE TO RELATED APPLICATIONS

This application claims the benefit of U.S. provisional application No. 60/591,037 filed Jul. 26, 2004.

BACKGROUND OF THE INVENTION

Tachykinins are a group of naturally occurring peptides found widely distributed throughout mammals, both within the central nervous system and in the peripheral nervous and circulatory systems. The three known mammalian tachykinins are Neurokinin-1 (NK-1, substance P), Neurokinin A, and Neurokinin B. These compounds act as neurotransmitters and immunomodulators and may contribute to the pathophysiology of a wide variety of human diseases.

Receptors for tachykinins have been identified and include neurokinin-1 (NK-1 or Substance P-preferring), NK-2 (Neurokinin A-preferring) and NK-3 (Neurokinin B-preferring). NK-1 receptor antagonists are being developed for the treatment of physiological conditions associated with an excess or imbalance of tachykinins, particularly substance P. Such conditions include affective disorders such as anxiety, depression, obsessive compulsive disorder, bulimia, and panic disorder. See Gentsch et al. *Behav. Brain Res.* 2002, 133, 363; Varty et al. *Neuropsychopharmacology* 2002, 27, 371; Papp et al. *Behav. Brain Res.* 2000, 115, 19; Kramer et al. *Science* 1998, 281, 1640; and Rosen et al. *Bioorg. Med. Chem. Lett.* 1998, 8, 281.

NK-1 antagonists are believed to modulate 5-HT function via noradrenergic pathways and have been shown to attenuate presynaptic 5-HT$_{1A}$ receptor function. Thus, the combination of serotonin reuptake inhibition with NK-1 antagonism may lead to new classes of drugs with improved characteristics.

Dual NK-1 antagonists-serotonin reuptake inhibitors have been reported. See Alvaro et al., PCT application WO 2004/005255; and Alvaro et al., PCT application WO 2004/005256; Ryckmans et al. *Bioorganic and Medicinal Chemistry Letters* 2002, 12, 261–264; MacLeod et al., U.S. Pat. No. 6,136,824.

DESCRIPTION OF THE INVENTION

The invention encompasses compounds of Formula I, including pharmaceutically acceptable salts and solvates, their pharmaceutical compositions, and their use in treating disorders associated with an excess or imbalance of tachykinins or serotonin or both.

One aspect of the invention are compounds of Formula I

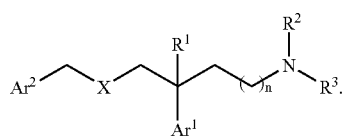

where:

Ar$^1$ is phenyl, naphthalenyl, or thienyl with 0–2 substituents selected from the group consisting of C$_{1-6}$alkyl, C$_{1-6}$alkoxy, trifluoromethyl, trifluoromethoxy, cyano, halo, and N(R$^4$)(R$^4$);

Ar$^2$ is phenyl substituted with 0–5 substituents selected from the group consisting of C$_{1-6}$alkyl, C$_{1-6}$alkoxy, trifluoromethyl, trifluoromethoxy, cyano, and halo;

R$^1$ is hydrogen, hydroxyl, C$_{1-6}$alkyl, or C$_{1-6}$alkoxy;

R$^2$ is hydrogen or C$_{1-6}$alkyl;

R$^3$ is hydrogen or C$_{1-6}$alkyl;

R$^4$ is hydrogen or C$_{1-6}$alkyl;

X is O, S, or NR$^4$; and n is 0 or 1;

or a pharmaceutically acceptable salt or solvate thereof.

Another aspect of the invention are compounds of Formula I where Ar$^1$ is phenyl substituted with 0–2 substituents selected from methyl, methoxy, or halo.

Another aspect of the invention are compounds of Formula I where Ar$^1$ is naphthalenyl or thienyl.

Another aspect of the invention are compounds of Formula I where Ar$^2$ is phenyl substituted with 0–2 substituents selected from the group consisting of C$_{1-6}$alkyl, C$_{1-6}$alkoxy, trifluoromethyl, trifluoromethoxy, cyano, and halo.

Another aspect of the invention are compounds of Formula I where Ar$^2$ is substituted with 2 substituents selected from the group consisting of methyl, halo and trifluoromethyl.

Another aspect of the invention are compounds of Formula I where where R$^1$ is hydrogen, methyl, or hydroxy.

Another aspect of the invention are compounds of Formula I where where R$^2$ and R$^3$ are independently hydrogen or methyl.

Another aspect of the invention are compounds of Formula I where where X is O.

Another aspect of the invention are compounds of Formula I where where n is 1.

Another aspect of the invention are compounds of Formula I with the following stereochemistry.

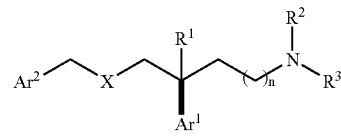

Another aspect of the invention are compounds of Formula I with the following stereochemistry.

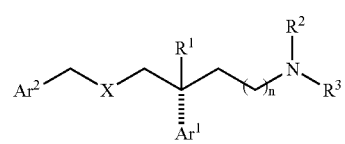

Any scope of variable Ar$^1$, Ar$^2$, R$^1$, R$^2$, R$^3$, R$^4$, X, and n can be used with any scope of any other variable.

"Alkyl," "alkoxy," and related terms with an alkyl portion include both straight and branched chain configurations. "Aryl" includes both carbocyclic and heterocyclic aromatic ring systems. "Thienyl" means the ring system derived from thiophene.

The invention includes all pharmaceutically acceptable salt forms of the compounds. Pharmaceutically acceptable salts are those in which the counter ions do not contribute significantly to the physiological activity or toxicity of the compounds and as such function as pharmacological equivalents. These salts can be made according to common organic techniques employing commercially available reagents. Some anionic salt forms include acetate, acistrate, besylate, bromide, chloride, citrate, fumarate, glucouronate, hydrobromide, hydrochloride, hydroiodide, iodide, lactate, maleate, mesylate, nitrate, pamoate, phosphate, succinate, sulfate, tartrate, tosylate, and xinofoate. Some cationic salt forms include ammonium, aluminum, benzathine, bismuth, calcium, choline, diethylamine, diethanolamine, lithium, magnesium, meglumine, 4-phenylcyclohexylamine, piperazine, potassium, sodium, tromethamine, and zinc.

The invention also includes all solvated forms of the compounds, particularly hydrates. Solvates do not contribute significantly to the physiological activity or toxicity of the compounds and as such function as pharmacological equivalents. Solvates may form in stoichiometric amounts or may form from adventitious solvent or a combination of both. One type of solvate is hydrate. Some hydrated forms include monohydrate, hemihydrate, and dihydrate.

Formula I compounds contain at least one asymmetric carbon atom, such as the carbon bearing $R^1$ (for example, see the compounds illustrated below). The invention includes all stereoisomeric forms of the compounds, both mixtures and separated isomers. Mixtures of stereoisomers can be separated into individual isomers by methods known in the art.

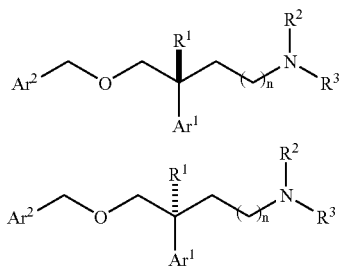

Synthetic Methods

Compounds of Formula I can be made according to methods known in the art including those illustrated in the schemes below. The formulas and variables illustrated in the schemes below are intended only to assist describing the synthesis of Formula I compounds and are not to be confused with the variables used to define Formula I compounds in the claims or in other sections of the specification.

Amino analogs 4 and dimethylamino analogs 5 can be synthesized according to Scheme 1. Cyano-ester 1 can be reduced to afford cyano-hydroxy intermediates 2. These intermediates can be alkylated to generate diaryl cyano intermediates 3. These intermediates can be reduced to yield amino analogs 4. Compounds 5 can be prepared by methylation of 4.

Scheme 1.

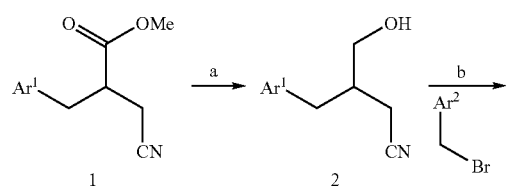

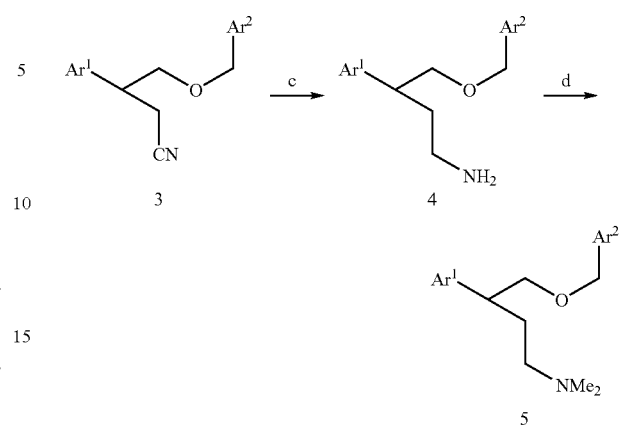

Reagents and conditions: a) LiBH$_4$, THF, rt, or 50° C.; b) arylmethyl bromide, NaH, DMF, rt; c) exc. BH$_3$—SMe$_2$, 80° C., THF, 3 h; d) 10 eq. formaldehyde, 37 wt. % in water, 10 eq. NaBH$_4$, MeOH, rt.

Monomethyl compounds 7 can be prepared following a two-step procedure (see Scheme 2). Compound 4 can be converted to carbamate 6 by treating with methyl chloroformate. Intermediate 6 can be reduced to afford amine 7.

Scheme 2.

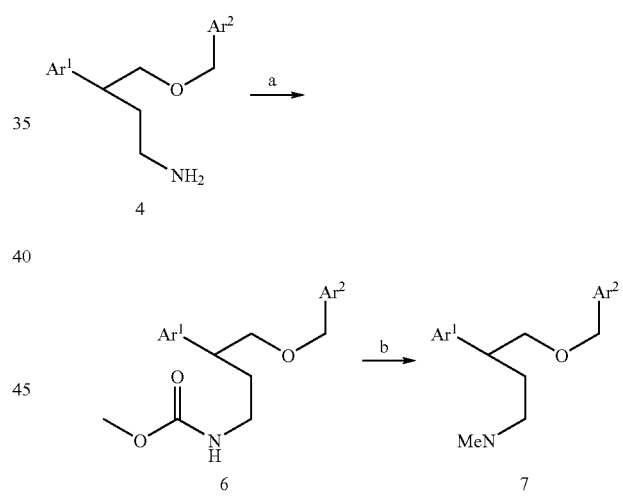

Reagents and conditions: (a) methyl chloroformate, K$_2$CO$_3$, CH$_2$Cl$_2$, rt; (b) LAH, THF, 90° C..

Methyl 3-cyano-2-phenylpropanoate can be prepared following the route shown in Scheme 3. DL-Tropic acid can be esterified-followed by mesylation and reaction with cyanide to afford the product.

Scheme 3.

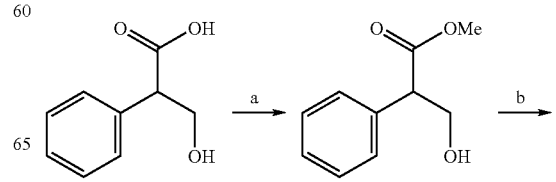

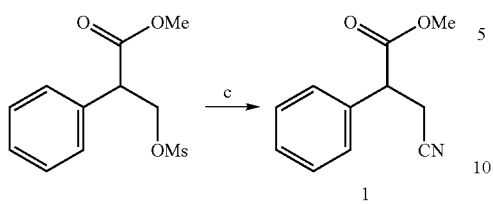

Reagents and conditions: (a) 2,2-dimethoxypropane, cat. TsOH, MeOH, reflux; (b) MsCl, Et₃NH, CH₂Cl₂, rt; (c) exc. NaCN, 12% Bu₄NCN, DMF, 80° C..

Other aryl intermediates 1 can be prepared by alkylating aryl- or hetero-aryl acetate with iodoacetonitrile or bromoacetonitrile following literature procedures (Scheme 4).

Scheme 4.

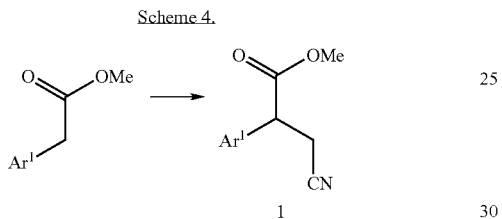

Other Formula I compounds can be synthesized from substituted aryl malonates following the route shown in Scheme 5. Thus, starting aryl malonates can be reduced to corresponding diols which can be monoalkylated. Oxidation of the monoalcohols can generate aldehydes which can be reductively aminated to generate some Formula I compounds.

Scheme 5.

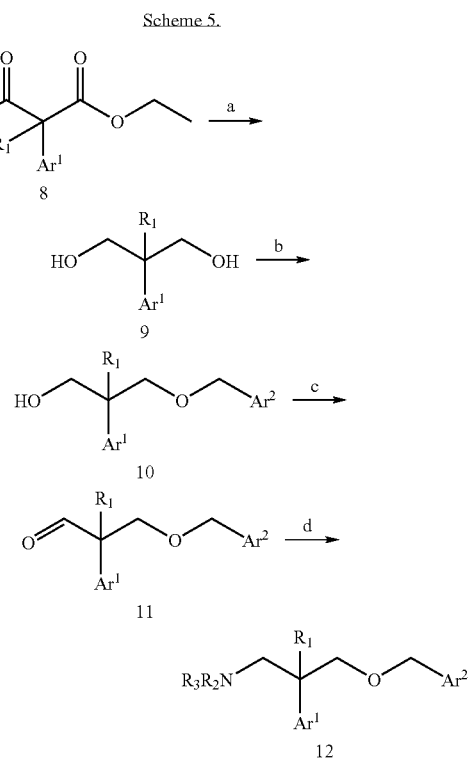

Reagents and conditions: (a) LAH, THF, -20° C.-rt; (b) NaH, DMF, arylmethyl bromide, rt; (c) xs Dess-Martin periodinane, CH₂Cl₂, rt; (d) MeNH₂, NaBH₄ or NH₃, NHMe₂, AcOH, NaBH(OAc)₃.

Other Formula I compounds can be made by according to Scheme 6. Alcohol 10 can be tosylated and displaced with cyanide. The resultant cyano compounds can be converted to amino, monmethylamino and dimethylamino compounds following the procedures described.

Scheme 6.

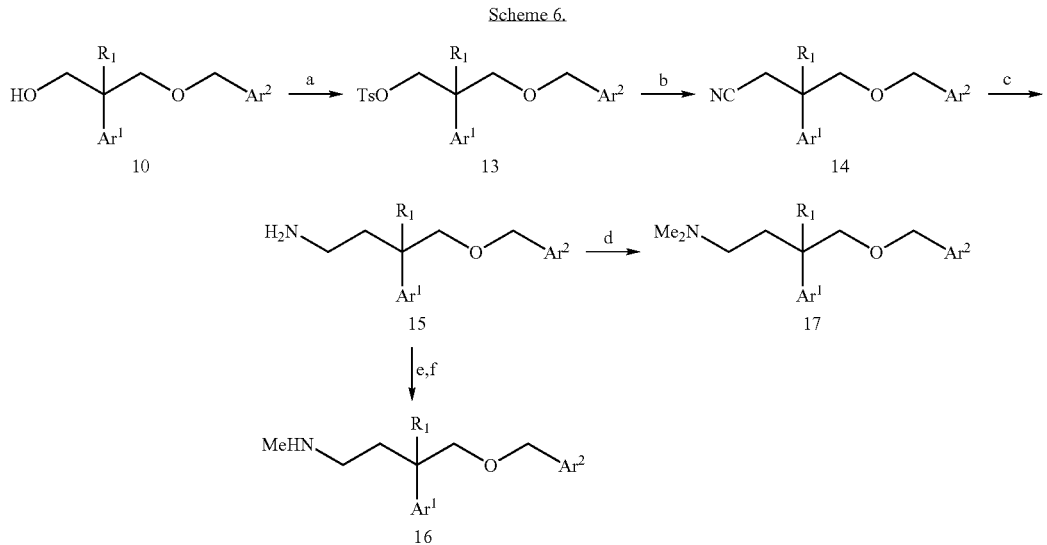

Reagents and conditions: (a) TsCl, Py, -20° C.-rt; (b) KCN, DMSO/H₂O, 100° C.; (c) BH₃—SMe₂, 80° C., THF; (d) 37% aq. formadehyde, NaBH₄; (e) methyl chloroformate, K₂CO₃, CH₂Cl₂, rt; (f) LAH, THF, 90° C..

Other Formula I compounds can be made according to Scheme 7. A benzyl alcohol as depicted in the scheme can be reacted with Weinreb acetamide 18 to give α-benzylated Weinreb acetamide 19. This amide can be reacted with a Grignard reagent to give ketone 20. The anion derived from acetonitrile can be added to ketone 20 and the subsequent product can be reduced to amine 22.

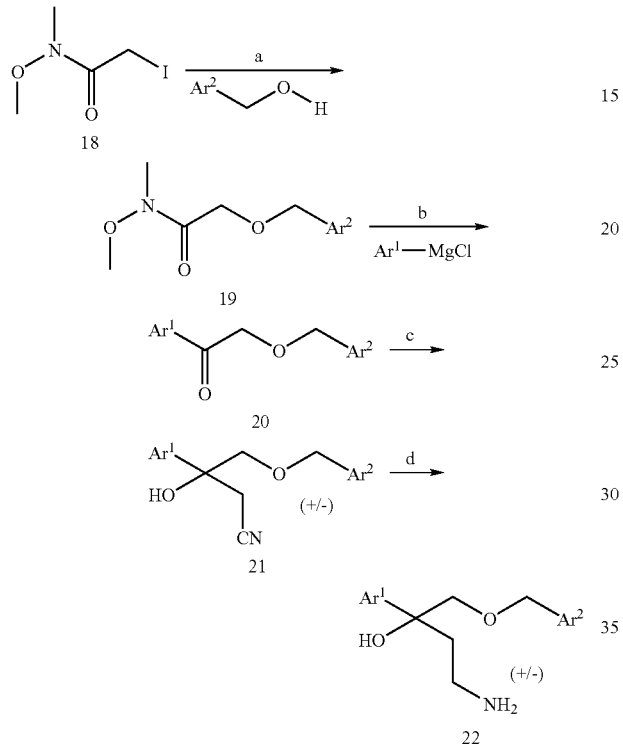

Reagents and conditions: (a) KN(TMS)2, THF, RT; (b) THF, RT; (c) LiCH2CN, THF, <-30° C.; (d) BH3—SMe2, RT.

Other compounds of Formula I can be synthesized from ketone 20 by treatment with trimethylsulfoxonium iodide to give epoxide 23 (Scheme 8). Reaction of 23 with an amine can generate amino alcohol 24.

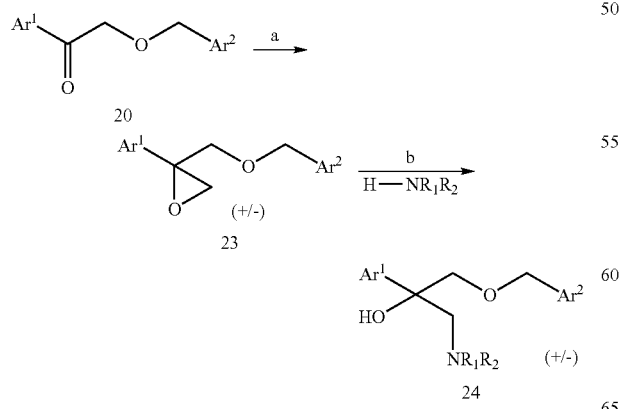

Reagents and conditions: (a) Me3SOI, NaH, DMSO, RT; (b) MeOH, 120° C..

Primary amine 22 can be reductively aminated to give amine 25 (Scheme 9).

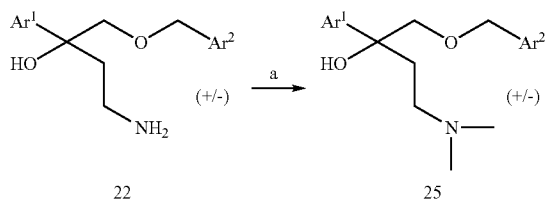

Reagents and conditions: (a) 37 wt. % HCHO (aq.), NaBH3(CN), RT.

Primary amine 22 can be acetylated, alkylated, and deacetylated to give amine 28 (Scheme 10);

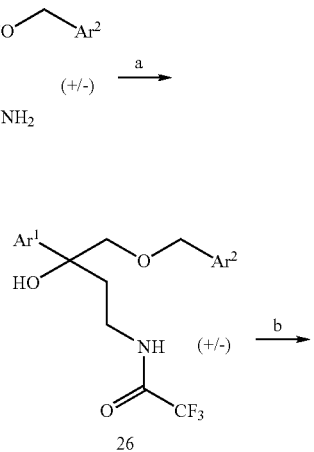

Reagents and conditions: (a) (CF3CO)2O, Et3N, CH2Cl2, RT; (b) MeI, K2CO3, acetone, 60° C.; (c) NH3, MeOH, RT.

Some thio compounds of Formula I can be made according to Scheme 11 and variations known in the art.

Scheme 11.

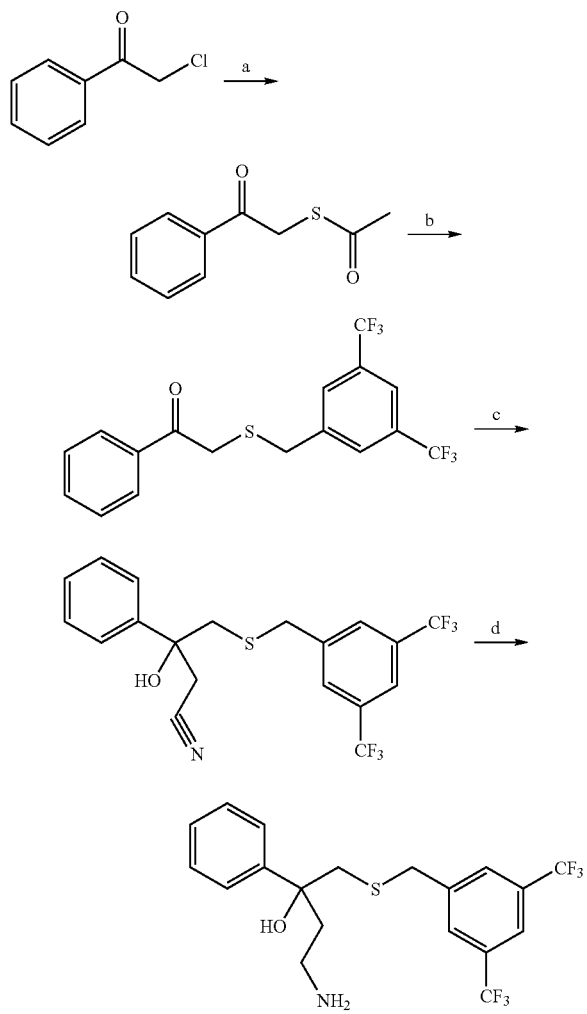

Reaction conditions: a) KSAc, acetone, RT; b) NaOMe, ArCH₂Br, methanol, -10° C.; c) LiCH₂CN, THF, <-30° C.; d) BH₃—SME₂, RT.

Some amino compounds of Formula I can be made according to Scheme 12 and variations known in the art.

Scheme 12.

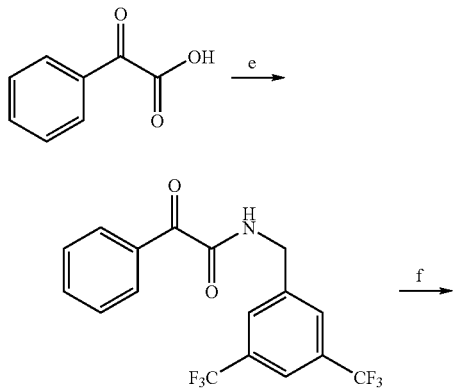

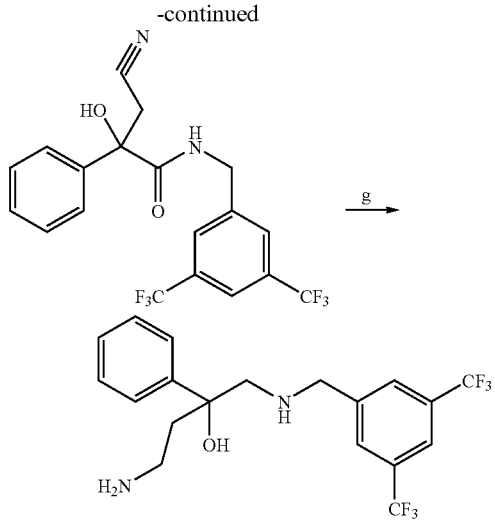

Reaction conditions: e) ArCH₂NH₂, DCC, 0° C. to RT; f) (i) NaH, TMSCl, 0° C.; then, (ii) LiCH₂CN, THF, <-30° C.; g) BH₃—SMe₂, RT.

Some compounds of Formula I can be prepared enantioselectively as outlined in Scheme 13. The ketone can be methylenated to afford a 1,1-disubstituted alkene. The resultant olefin can be converted to an optically-active diol using an asymmetric dihydroxylation. The primary hydroxyl can be selectively protected as its pivaloate ester. The tertiary hydroxyl can then be converted to a silyl ether by treatment with triethylsilyl trifluoromethanesuflonate in the presence of 2,6-lutidine. The pivaloate ester can then be cleaved by the action of diisobutylaluminum hydride. The resultant alcohol can be oxidized to afford an aldehyde which can be condensed with nitromethane to afford a nitroalkene. The nitroalkene can be reduced to afford a primary amine. Cleavage of the silyl ether affords an optically-active Formula I compound.

Scheme 13.

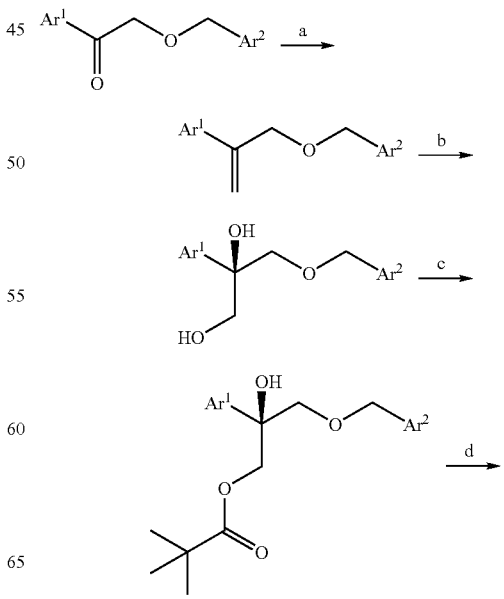

-continued

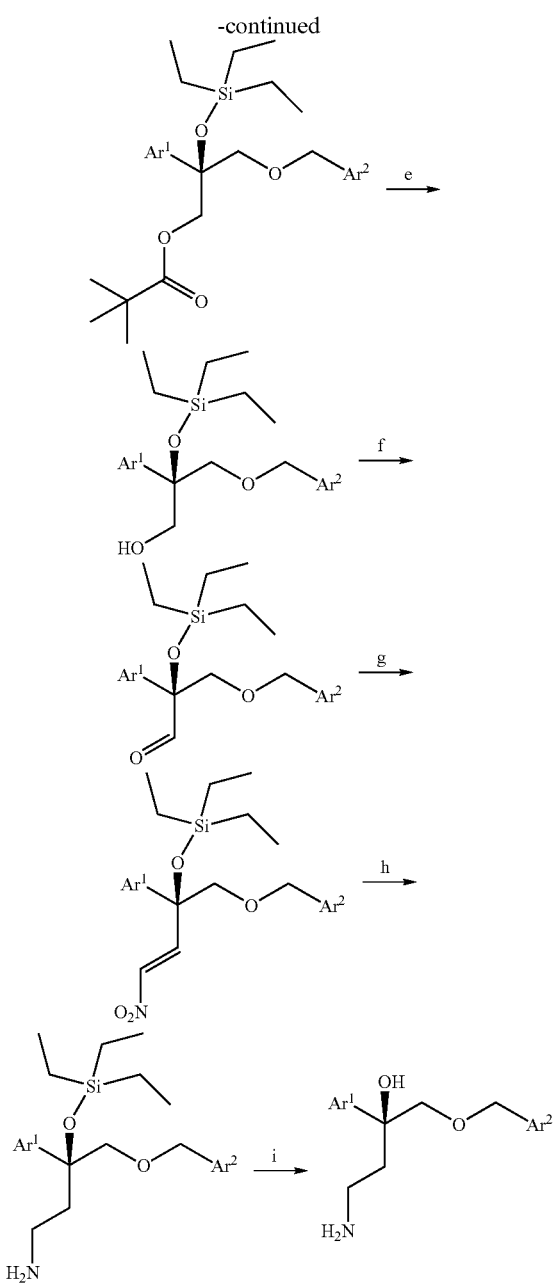

Reagents and conditions:
(a) methyltriphenylphosphonium bromide, BuLi, THF, 0° C.-rt;
(b) AD-mix-β, t-BuOH/H₂O, 0° C.-rt;
(c) pivaloyl chloride, pyr, CH₂Cl₂, -78° C.– -60° C.;
(d) TESOTf, 2,6-lutidine, CH₂Cl₂, -78° C.–0° C.;
(e) DIBAL, CH₂Cl₂, -78° C.;
(f) 3,3,3-triacetoxy-3-iodophthalide, CH₂Cl₂, rt;
g) MeNO₂, LiOt-Bu, t-BuOH, rt; then MsCl, pyr, Et₃N, CH₂Cl₂, 0° C.-rt;
(h) PtO₂, H₂, MeOH;
(i) TBAF, THF, rt.

Biological Methods

NK-1 Binding assay. U373 cells, a human glioblastoma-astrocytoma cell line that endogenously expresses the neurokinin-1 (NK-1) receptor, were grown in a monolayer culture at 37° C. in 5% $CO_2$ and fed with Minimum Essential Medium (MEM) supplemented with 10% fetal bovine serum. Membranes were prepared as follows: Cells were washed twice with ice-cold phosphate-buffered saline (pH 7.4) and then incubated for 5–10 minutes with ice-cold 10 mM Tris buffer (pH 7.4) containing 5 mM EDTA. Cells were removed from plates, homogenized, and centrifuged at 32,000×g for 20 minutes. The resulting supernatant was discarded, and the pellet resuspended by homogenization in 50 mM Tris buffer (pH 7.4) containing 1 mM EDTA and centrifuged at 32,000×g for 20 minutes. The resulting supernatant was discarded, and the pellet resuspended by homogenization in NK-1 binding assay buffer (50 mM Tris-HCL (pH 7.4), 3 mM MnCl2, 200 μg/ml BSA, 5 μg/ml chymostatin, 40 μg/ml bacitracin and 4 μg/ml leupeptin).

On the day of an experiment the membrane preparation was thawed, homogenized and diluted with NK-1 binding assay buffer to the appropriate concentration. Competition binding assays were performed in 96 well plate format by incubating membranes (5–10 μg/well) with Bolton Hunter labeled [$^{125}$I] Substance P, at a concentration of 200 nM, and concentrations of drugs ranging from 10000 to 0.01 nM. Samples were incubated for 30 min at 20° C. then filtered through GF/B glass fiber filters (pretreated with 1% polyethyleneimine and 0.3% Triton X-100) using a Brandel cell harvester. The filters were then washed with 10 ml ice cold 50 mM Tris-HCL (pH 7.4) containing 3 mM $MgCl_2$. Non-specific was defined in the presence of 2 μM L-733,060 (a non-peptide NK-1 antagonist). The amount of radioligand bound in the presence and absence of competitor was analyzed by plotting (–)log drug concentration versus the amount of radioligand specifically bound. The midpoint of the displacement curve ($IC_{50}$, nM), signifies the potency. Ki values can be calculated using the method of Cheng and Prusoff (Cheng and Prusoff, *Biochemical Pharmacology*, Vol 22, pp. 3099–3108, Pergamon Press (1973)).

Serotonin transporter binding assay. HEK-293 cells that stably express human serotonin transporters (HEK-hSERT cells) were grown at 37° C. in 5% $CO_2$ as a monolayer in medium consisting of EMEM supplemented with 10% fetal bovine serum and G418 sulfate (500 μg/ml). To prepare membranes for radioligand binding experiments, cells were rinsed twice with phosphate-buffered saline (138 mM NaCl, 4.1 mM KCl, 5.1 mM $Na_2PO_4$, 1.5 mM $KH_2PO_4$, 11.1 mM glucose, pH 7.4). Cells were transferred from plates to polypropylene tubes (16×100 mm), centrifuged at 1,200×g for 5 min and were frozen at –80° C. until assay. Following centrifugation, pellets were resuspended by homogenization in buffer consisting of 50 mM Tris (pH 7.7 at 25° C.), 120 mM NaCl and 5 mM KCl and then centrifuged at 32,000×g for 10 min. Following centrifugation, supernatants were discarded and pellets were resuspended in buffer consisting of 50 mM Tris (pH 7.4 at 25° C.), 150 mM NaCl and 5 mM KCl. Membrane homogenates (200 μl/plate) were incubated with 1 nM [$^3$H]-citalopram (specific activity=85 Ci/mmol) and increasing concentrations of test compounds for 1 hr at 25° C. in a total volume of 250 μl. The assay buffer consisted of 50 mM Tris (pH 7.4 at 25° C.), 120 mM NaCl and 5 mM KCl (pH 7.4 with conc. HCl). Plates were incubated for 1 hr at 25° C., then filtered through 0.5% PEI treated Whatman GF/B filters using a Brandel cell harvester. Filters were washed three times with 3 ml of ice-cold tris wash buffer. Non-specific binding was defined with 10 μM fluoxetine. Amount of radioligand bound in the presence and absence of competitor was analyzed by plotting (–)log drug concentration versus the amount of radioligand specifically bound. The midpoint of the displacement curve ($IC_{50}$, nM), signifies the potency. Ki values can be calculated using the method of Cheng and Prusoff (Cheng and Prusoff, *Biochemical Phar-* macology, Vol 22, pp. 3099–3108, Pergamon Press (1973)). NK-1 and serotonin transporter binding results are shown in Table 1.

TABLE 1

| Example | NK-1 IC$_{50}$ (nM) | SERT IC$_{50}$ (nM) |
|---|---|---|
| 1 | A | B |
| 2 | A | A |
| 3 | A | B |
| 4 | A | A |
| 5 | A | C |
| 6 | A | A |
| 7 | B | C |
| 8 | A | A |
| 9 | A | A |
| 10 | A | B |
| 11 | B | A |
| 12 | A | A |
| 13 | A | A |
| 14 | A | A |
| 15 | A | A |
| 16 | C | C |
| 17 | A | A |
| 18 | A | A |
| 19 | A | B |
| 20 | B | A |
| 21 | A | A |
| 22 | B | A |
| 23 | A | A |
| 24 | A | B |
| 25 | A | B |
| 26 | A | A |
| 27 | B | A |
| 28 | B | A |
| 29 | A | A |
| 30 | A | A |
| 31 | A | A |
| 32 | A | A |
| 33 | A | A |
| 34 | A | A |
| 35 | C | B |
| 36 | A | A |
| 37 | A | A |
| 38 | B | A |
| 39 | B | A |
| 40 | A | A |
| 41 | A | A |
| 42 | A | A |
| 43 | A | A |
| 44 | A | A |
| 45 | A | A |
| 46 | C | A |
| 47 | C | C |
| 48 | C | A |
| 49 | C | C |
| 50 | C | A |
| 51 | A | A |
| 52 | C | A |
| 53 | A | A |
| 54 | C | A |
| 55 | B | B |
| 56 | C | B |
| 57 | C | C |
| 58 | C | B |
| 59 | C | B |
| 60 | C | A |
| 61 | A | A |
| 62 | C | A |
| 63 | C | A |
| 64 | B | A |
| 65 | C | A |
| 66 | C | B |
| 67 | C | B |
| 68 | A | A |
| 69 | C | A |
| 70 | C | A |
| 71 | A | B |
| 72 | A | A |
| 73 | A | A |
| 74 | A | A |
| 75 | A | B |
| 76 | B | A |
| 77 | B | B |
| 78 | B | B |
| 79 | A | A |
| 80 | B | A |
| 81 | B | — |

IC$_{50}$ values: A = 1–100 nM; B = 100–300 nM; C >300 nM.

Pharmaceutical Composition and Methods of Use

The compounds of Formula I demonstrate inhibition of neurokinin-1 or serotonin reuptake or both. Inhibition of these receptors correlates with efficacy for affective disorders such as anxiety, depression, obsessive compulsive disorder, bulimia, and panic disorder. As such, the compounds of Formula I can be useful for the treatment of these disorders and other aspects of the invention are compositions and methods of using the compounds to treat these conditions and other conditions associated with aberrant levels of tachykinins or serotonin or both.

The compounds of this invention are generally given as pharmaceutical compositions comprised of a therapeutically effective amount of a compound of Formula I, or a pharmaceutically acceptable salt, and a pharmaceutically acceptable carrier and may contain conventional excipients. A therapeutically effective amount is the amount needed to provide a meaningful patient benefit as determined by practitioners in that art. Pharmaceutically acceptable carriers are those conventionally known carriers having acceptable safety profiles. Compositions encompass all common solid and liquid forms including capsules, tablets, losenges, and powders as well as liquid suspensions, syrups, elixers, and solutions. Compositions are made using common formulation techniques and conventional excipients (such as binding and wetting agents) and vehicles (such as water and alcohols).

Solid compositions are normally formulated in dosage units providing from about 1 to about 1000 mg of the active ingredient per dose. Some examples of solid dosage units are 1 mg, 10 mg, 100 mg, 250 mg, 500 mg, and 1000 mg. Liquid compositions are generally in a unit dosage range of 1–100 mg/mL. Some examples of liquid dosage units are 1 mg/mL, 10 mg/mL, 25 mg/mL, 50 mg/mL, and 100 mg/mL. Generally, the dosage unit will be in a unit range similar to agents of that class used clinically, for example fluoxetine.

The invention encompasses all conventional modes of administration; oral and parenteral methods are preferred. Generally, the dosing regimen will be similar to agents of that class used clinically, for example fluoxetine. Typically, the daily dose will be 0.01–100 mg/kg body weight daily. Generally, more compound is required orally and less parenterally. The specific dosing regime, however, should be determined by a physician using sound medical judgement.

Tachykinin and serotonin modulators are associated with depression. Accordingly, another aspect of the invention are methods for treating depressive disorders including Major Depressive Disorders (MDD), bipolar depression, unipolar depression, single or recurrent major depressive episodes, recurrent brief depression, catatonic features, melancholic features including feeding disorders, such as anorexia, weight loss, atypical features, anxious depression, or postpartum onset. Other central nervous system disorders encompassed within the term MDD include neurotic depression, post-traumatic stress disorders (PTSD) and social phobia, with early or late onset dementia of the Alzheimer's type, with depressed mood, vascular dementia with depressed mood, mood disorders and tolerance induced by drugs such as alcohol, amphetamines, cocaine, inhalants, opioids, sedatives, anxiolytics and other substances, schizoaffective disorder of the depressed type, and adjustment disorder with depressed mood.

Tachykinin and serotonin modulators are also associated with the treatment or prevention of schizophrenic disorders. Accordingly, another aspect of the invention are methods for treating schizophrenic disorders including paranoid schizophrenia, disorganized schizophrenia, catatonic schizophrenia, undifferentiated schizophrenia, residual schizophrenia.

Tachykinin and serotonin modulators are also associated with the treatment or prevention of anxiety. Accordingly, another aspect of the invention are methods for treating anxiety disorders including panic disorders, agoraphobia, phobias, obsessive-compulsive disorder, stress disorders including post-traumatic stress disorders, generalized anxiety disorders, acute stress disorders and mixed anxiety-depression disorders.

Tachykinin and serotonin modulators are also associated with the treatment or prevention of cognitive disorders. Accordingly, another aspect of the invention are methods for treating cognitive disorders including dementia, and amnesia disorders. Tachykinin and serotonin modulators are also associated with the treatment or prevention of memory and cognition in healthy humans.

Tachykinin and serotonin modulators are also associated with use as analgesics. Accordingly, another aspect of the invention are methods for treating pain, including the treatment of traumatic pain such as postoperative pain, chronic pain such as arthritic pain such as occurring in osteo-, rheumatoid or psoriatic arthritis, neuropathic pain such as post-herpetic neuralgia, trigeminal neuralgia, segmental or intercostal neuralgia, fibromyalgia, peripheral neuropathy, diabetic neuropathy, chemotherapy-induced neuropathy, AIDS-related neuropathy, various forms of headache such as migraine, acute or chronic tension headache, cluster headaches, maxillary sinus pain, cancer pain, pain of bodily origin, gastrointestinal pain, sport's injury pain, dysmennorrhoea, menstrual pain, meningitis, musculoskeletal pain, low back pain e.g. spinal stenosis, prolapsed disc, sciatica, angina, ankylosing spondyolitis, gout, burns, scar pain, itch and thalamic pain such as post stroke thalamic pain.

Tachykinin and serotonin modulators are also associated with the treatment or prevention of sleep disorders. Accordingly, another aspect of the invention are methods for treating sleep disorders including insomnia, sleep apnea, narcolepsy, and circadian rhymic disorders.

Tachykinin and serotonin modulators are also associated with the treatment or prevention of inflammation. Accordingly, another aspect of the invention are methods for treating inflammation, including the treatment of inflammation in asthma, influenza and chronic bronchitis, in the treatment of inflammatory diseases of the gastrointestinal tract such as Crohn's disease, ulcerative colitis, inflammatory bowel disease and non-steroidal anti-inflammatory drug induced damage, inflammatory diseases of the skin such as herpes and eczema, inflammatory diseases of the bladder such as cystitis and urge incontinence, and eye and dental inflammation.

Tachykinin and serotonin modulators are also associated with the treatment or prevention of allergic disorders.

Accordingly, another aspect of the invention are methods for treating allergic disorders, in particular allergic disorders of the skin such as urticaria, and allergic disorders of the airways such as rhinitis.

Tachykinin and serotonin modulators are also associated with the treatment or prevention of emesis, nausea, retching and vomiting. Accordingly, another aspect of the invention are methods for treating these disorders.

Tachykinin and serotonin modulators are also associated with the treatment or prevention of premenstrual dysphoric disorder (PMDD), in chronic fatigue syndrome and multiple sclerosis. Accordingly, another aspect of the invention are methods for treating these disorders.

DESCRIPTION OF SPECIFIC EMBODIMENTS

Intermediate 1

Methyl 3-cyano-2-phenylpropanoate: DL-tropic acid (10 g, 120 mmol), 2,2-dimethoxypropane (12.48 g, 120 mmol) and catalytical amount of p-toluenesulfonic acid (100 mg) were mixed in MeOH (50 ml) and refluxed overnight. The reaction mixture was cooled and concentrated in-vacuo to dryness and then dissolved in ethyl acetate. The organic phase was washed with water, brine and dried with sodium sulfate, and concentrated in-vacuo to dryness. The crude product was dissolved in anhydrous mentylene chloride (150 ml). Triethylamine (7.27 g, 72 mmol) and methanesulfonyl chloride (8.24 g, 72 mmol) were added and stirred at room temperature overnight before it was washed with water, brine and dried with sodium sulfate. The concentrated residue was heated with KCN (5.88 g, 120 mmol) and tetrabutylammonium cyanide (2 g, 7.4 mmol) in DMF at 80° C. for 1 hour. After cooled down to room temperature, reaction mixture was diluted with methylene chloride, washed with water, brine and dried with $Na_2SO_4$. After concentration in-vacuo, the crude product was purified by silica flash chromatography (10% ethyl acetate in hexanes) to afford 6.4 g of the desired product as a yellowish solid (58% in three steps). $^1$H NMR (500 MHz, $CDCl_3$) δ: 7.37 (m, 3 H), 7.27 (m, 2 H), 3.94 (t, J=7.63 Hz, 1 H), 3.73 (s, 3 H), 3.04 (dd, J=16.79, 7.63 Hz, 1 H), 2.81 (dd, J=17.09, 7.63 Hz, 1H).

Intermediate 2

4-(3,5-bis(trifluoromethyl)benzyloxy)-3-phenylbutanenitrile: Methyl 3-cyano-2-phenylpropanoate (350 mg, 1.90 mmol) was treated with LiBH4 (2.28 mmol) in THF (20 ml) at 50° C. for 2 hours until completion of the reaction. It was quenched with water and extracted with ethyl acetate. The organic phase was washed with water, brine and dried with $Na_2SO_4$ before being concentrated to dryness. The crude product was then mixed with 3,5-bis(trifluoromethyl)benzyl bromide in DMF (20 ml) and sodium hydride (91 mg, 2.28 mmol) was added. The reaction mixture was stirred at room temperature for 30 minutes and quenched with water, and extracted with ethyl acetate. The organic phase was washed with water, brine and concentrated. The crude residue was purified by silica flash chromatography (15% ethyl acetate in hexanes) to afford the desired product (405 mg, 55% in two steps). $^1$H NMR (500 MHz, $CDCl_3$) δ ppm 2.78 (dd, J=116.79, 7.32 Hz, 1 H) 2.88 (m, 1 H) 3.33 (m, 1 H) 3.81 (m, 2 H) 4.65 (s, 2 H) 7.27 (m, 2 H) 7.31 (m, 1 H) 7.37 (m, 2 H) 7.73 (s, 2 H) 7.80 (s, 1 H).

Intermediate 9

2-Methyl-2-phenylpropane-1,3-diol: Diethyl diphenylmalonate (10 g, 42.4 mmol) and iodomethane (6.6 g, 46.6 mmol) was mixed in anhydrous THF (200 ml) at room temperature before NaH powder was added in several portions. The reaction finished instantly with release of heat. After cooled down to room temperature, aqueous $NaHCO_3$ solution was added to quench the reaction. The mixture was extracted with ethyl acetate, washed with water, brine, dried with $Na_2SO_4$ and concentrated. A clean NMR spectrum of the crude product identified it as the desired product. $^1H$ NMR (500 MHz, $CDCl_3$) δ ppm 1.26 (t, J=7.17 Hz, 6 H) 4.24 (m, 3 H) 7.34 (m, 5 H). The crude product was then dissolved in anhydrous THF (200 ml) and cooled to −20° C. Lithium aluminun hydride (42.4 mmol) was added via dropping funnel within 10 minutes. The reaction mixture was warmed up naturally to room temperature and quenched with ethyl acetate and water. The organic layer was washed with brine and dried with $Na_2SO_4$ before being concentrated in-vacuo. The crude product was purified by silica flash chromatography using 50% ethyl acetate in hexanes to yield 4.35 grams (62% in two steps) of the desired product. $^1H$ NMR (500 MHz, $CDCl_3$) δ: 3.85 (m, 3 H) 3.98 (d, J=10.99 Hz, 2 H) 7.27 (m, 1 H) 7.38 (t, J=7.93 Hz, 2 H) 7.44 (m, 2 H).

Intermediate 10

3-(3,5-bis(trifluoromethyl)benzyloxy)-2-methyl-2-phenylpropan-1-ol: 2-Methyl-2-phenylpropane-1,3-diol (3.37 g, 20.3 mmol) was dissolved in DMF, NaH (812 mg, 60%, 20.3 mmol) was added and the mixture was stirred at room temperature for 30 minutes. A DMF solution of 3,5-bistrifluoromethylbenzyl bromide (6.23 g, 20.3 mmol) was added in one portion and stirred for another 1 hour before it was quenched with water and extracted with ethyl acetate. The organic phase was washed with brine and dried with $Na_2SO_4$ before being concentrated. The crude product was purified by silica flash chromatography using 15% ethyl acetate in hexanes to yield 4.2 grams (52.8%) of the desired monoalkylated product. $^1H$ NMR (500 MHz, $CDCl_3$) δ: 1.40 (s, 3 H) 1.78 (s, 1 H) 3.72 (d, J=9.16 Hz, 1 H) 3.82 (d, J=9.16 Hz, 1 H) 3.89 (m, 2 H) 4.64 (s, 2 H) 7.26 (m, 1 H) 7.37 (m, 4 H) 7.72 (s, 2 H) 7.79 (s, 1 H).

Intermediate 11

3-(3,5-bis(trifluoromethyl)benzyloxy)-2-methyl-2-phenylpropanal: 3-(3,5-bis(trifluoromethyl)benzyloxy)-2-methyl-2-phenylpropan-1-ol (500 mg, 1.28 mol) was treated with Dess-Martin periodinane (5.76 g, 15 wt % in $CH_2Cl_2$, 2.03 mmol) in methylene chloride for 2 hour at room temperature. The reaction mixture was loaded directly onto silica column and eluted with 5% ethyl acetate in haxanes. 375 mg (75%) of the desired aldehyde was obtained. $^1H$ NMR (500 MHz, $CDCl_3$) δ: 1.60 (s, 3 H) 3.80 (m, 1 H) 4.02 (m, 1 H) 4.62 (m, 2 H) 7.27 (m, 2 H) 7.33 (m, 1 H) 7.39 (m, 2 H) 7.67 (s, 2 H) 7.78 (s, 1 H) 9.61 (s, 1 H).

Intermediate 13

3-(3,5-bis(trifluoromethyl)benzyloxy)-2-methyl-2-phenylpropyl 4-methylbenzenesulfonate: 3-(3,5-bis(trifluoromethyl)benzyloxy)-2-methyl-2-phenylpropan-1-ol (1.72 g, 4.39 mmol) was mixed with pyridine (1.39 g, 17.6 mmol) in anhydrous methylene chloride (20 ml) and cooled to −20° C. Solid p-toluenesulfonyl chloride (3.35 g, 17.6 mmol) was added in one portion and the mixture was warmed up naturally to room temperature and stirred overnight. The mixture was then loaded directly onto silica column and eluted with 5% ethyl aceta in hexanes. 1.89 g (79%) of the desired product was obtained. $^1H$ NMR (500 MHz, $CDCl_3$) δ: 1.37 (s, 3 H) 2.38 (s, 3 H) 3.66 (d, J=2.75 Hz, 2 H) 4.21 (d, J=9.46 Hz, 1 H) 4.27 (d, J=9.46 Hz, 1 H) 4.52 (s, 2 H) 7.27 (m, 5 H) 7.35 (d, J=8.24 Hz, 2 H) 7.62 (s, 2 H) 7.70 (s, 1 H) 7.80 (d, J=8.24 Hz, 2 H).

Intermediate 14

4-(3,5-bis(trifluoromethyl)benzyloxy)-3-methyl-3-phenylbutanenitrile: Potassium cyanide (476 mg, 7.33 mmol) was wet by small amount of water (100 ul) and then dimethylsulfoxide (2 ml) was added. A dimethylsulfoxide solution of 3-(3,5-bis(trifluoromethyl)benzyloxy)-2-methyl-2-phenylpropyl 4-methylbenzenesulfonate (400 mg, 0.733 mmol) was added and heated up to 100° C. overnight. After cooled to room temperature the reaction mixture was directly loaded onto silica column and eluted with 20% ethylacetate in hexanes to give 46.2 mg of the desired product. $^1H$ NMR (300 MHz, $CDCl_3$) δ ppm 1.55 (s, 3 H) 3.01 (m, 2 H) 3.74 (m, 2 H) 4.69 (s, 2 H) 7.30 (m, 1 H) 7.38 (m, 2 H) 7.46 (m, 2 H) 7.84 (s, 2 H) 7.87 (s, 1 H).

Intermediate 23

2-((3,5-bis(trifluoromethyl)benzyloxy)methyl)-2-phenyloxirane: Trimethylsulfoxonium iodide (185 mg, 0.84 mmol) was dissolved in anhydrous dimethylsulfoxide (2 ml). Sodium hydride (60 wt % in mineral oil, 36 mg, 0.9 mmol) was added to the solution and followed by addition of (2-(3,5-bis(trifluoromethyl)benzyloxy)-1-phenylethanone). After stirred for 1 hour, the reaction mixture was diluted with ethyl acetate and washed with brine. The organic layer was dried with magnesium sulfate, concentrated, and the residue was purified by flash chromatography on silica gel to give the desired product. $^1H$ NMR (500 MHz, CHLOROFORM-D) δ ppm 7.76 (s, 1 H) 7.69 (s, 2 H) 7.40–7.45 (m, 2 H) 7.34–7.39 (m, 2 H) 7.30–7.34 (m, 1 H) 4.65–4.72 (m, 2 H) 4.23 (d, J=11.90 Hz, 1 H) 3.79 (d, J=11.60 Hz, 1 H) 3.11 (d, J=5.19 Hz, 1 H) 2.82 (d, J=5.19 Hz, 1 H); LRMS [ESI, $MNa^+$] m/z calcd for $C_{18}H_{14}O_2F_6Na$ 399.08, found 398.97.

(2-(3,5-bis(trifluoromethyl)benzyloxy)-1-phenylethanone) was prepared as in General Method A, by using starting reagents (3,5-bis(trifluoromethyl)phenyl)methanol and phenylmagnesium chloride.

Intermediate 26

N-(4-(3,5-bis(trifluoromethyl)benzyloxy)-3-hydroxy-3-phenylbutyl)-2,2,2-trifluoroacetamide: 1-(3,5-bis(trifluoromethyl)benzyloxy)-4-amino-2-phenylbutan-2-ol TFA salt (37 mg, 0.071 mmol) was dissolved in 1,2-dichloroethane (0.6 ml). Triethylamine (0.040 ml, 0.29 mmol) was added to the solution, and followed by addition of trifluoroacetic anhydride (0.013 ml, 0.091 mmol) and catalytic amount of 4-dimethylaminopyridine. After stirred overnight at room temperature, the reaction mixture was concentrated, and the residue was purified by flash chromatography on silica gel to give the desired trifluoroacetamide. $^1H$ NMR (300 MHz, Acetone) δ ppm 8.27 (s, 1 H) 7.95 (s, 2 H) 7.94 (s, 1 H) 7.54–7.61 (m, 2 H) 7.31–7.40 (m, 2 H) 7.23–7.31 (m, 1 H) 4.72–4.84 (m, 2 H) 4.69 (s, 1 H) 3.73–3.84 (m, 2 H)

3.29–3.43 (m, 1 H) 3.19 (ddd, J=19.39, 8.05, 5.86 Hz, 1 H) 2.27 (ddd, J=8.60, 6.40, 4.39 Hz, 2 H); LRMS [ESI, MNa$^+$] m/z calcd for $C_{21}H_{18}NO_3F_9Na$ 526.10, found 525.97.

1-(3,5-bis(trifluoromethyl)benzyloxy)-4-amino-2-phenylbutan-2-ol TFA salt was prepared as in General A, by using starting reagents (3,5-bis(trifluoromethyl)phenyl) methanol and phenylmagnesium chloride.

Intermediate 27

N-(4-(3,5-bis(trifluoromethyl)benzyloxy)-3-hydroxy-3-phenylbutyl)-2,2,2-trifluoro-N-methylacetamide: Excess amount of potassium carbonate (150 mg, 1.1 mmol) and excess amount of methyl iodide (0.040 ml, 0.064 mmol) were mixed with N-(4-(3,5-bis(trifluoromethyl)benzyloxy)-3-hydroxy-3-phenylbutyl)-2,2,2-trifluoroacetamide (15 mg, 0.030 mmol) in acetone (2 ml). The reaction mixture was heated in microwave at 60° C. for 10 minutes. The salt precipitate was filtered off and the filtrate was concentrated. The residue was purified by preparative HPLC to give the desired N-methylacetamide. $^1$H NMR (300 MHz, MeOH) δ ppm 7.84 (s, 3 H) 7.46–7.54 (m, 2 H) 7.35 (ddd, J=8.14, 6.50, 4.76 Hz, 2 H) 7.22–7.30 (m, 1 H) 4.61–4.73 (m, 2 H) 3.62–3.75 (m, 2 H) 3.40–3.55 (m, 1 H) 3.11–3.37 (m, 1 H) 3.01 (s, 2 H) 2.93 (s, 1 H) 2.15–2.31 (m, 2 H); LRMS [ESI, (MH$^+$–H$_2$O)] m/z calcd for $C_{22}H_{19}NO_2F_9$ 500.13, found 499.97.

General Method A for Scheme 7

Intermediate 19

α-benzylated acetamides: A benzyl alcohol solution in anhydrous THF (0.5 M, 2 ml, 1.0 mmol) were cooled to 0° C. Potassium bis(trimethylsilyl)amide (0.91 M in THF, 1.5 ml, 1.4 mmol) was added drop-wise and the reaction mixtures were stirred for 1 hour at 0° C. 2-Iodo-N-methoxy-N-methylacetamide (0.5 M in THF, 2 ml, 1.0 mmol) was then added drop-wise to the above mixtures. The resultant reaction mixtures were allowed to warm to room temperature and stirred overnight. The salt precipitates were filtered off and the filtrates were concentrated. The residues were purified by flash chromatography on silica gel to give α-benzylated acetamides 19.

Intermediate 20

Ketones: α-Benzylated acetamides 19 (0.14–0.35 mmol) obtained above were dissolved in anhydrous THF (2 ml). 2 equivalents of aromatic Grignard reagents or aromatic lithium reagents (0.28–0.70 mmol) were added drop-wise. The reaction mixtures were stirred at room temperature for 10 minutes before $CH_2Cl_2$ (2 ml) and MeOH (1 ml) were added to quench the reaction. The mixtures were filtered through pads of silica gel in parallel and the silica pads were rinsed with ethyl acetate. The combined filtrates were concentrated and the residues were purified by flash chromatography on silica to give ketones 20.

Intermediate 21

Nitriles: n-Butyllithium in hexanes (2.5 M, 36 ml, 90 mmol) was added to anhydrous THF (600 ml) at −78° C. Acetonitrile (4.0 ml, 76 mmol) was added to the above solution slowly. The reaction mixture was stirred at −78° C. for 15 min, warmed to −40° C. for 15 minutes, and then cooled to −78° C. Ketones 20 in anhydrous THF (2 ml, 0.08–0.3 mmol) were added to 1.3 equivalent of the above lithium acetonitrile solution (0.12 M in THF, 0.9–3.3 ml) and the resultant mixtures were allowed to warm to room temperature. The reactions were quenched by addition of aqueous ammonium chloride solution and were extracted with ethyl acetate. The organic layers were washed with brine and concentrated. The residues were purified by flash chromatography on silica gel to give the nitrile intermediates 21.

Intermediate 22

Primary amines TFA salt: nitriles 21 (0.03–1.76 mmol) was dissolved in excess amount of borane dimethylsulfide complex (0.5–3 ml, 5.3–32 mmol). The solution was stirred at room temperature for 2 hours. The excess borane dimethylsulfide complex was removed and the residue was carefully quenched by slow addition of small amount of methanol, and purified by preparative HPLC to give the desired primary amine as a TFA salt.

Intermediate 29

α-Thioacetyl acetophenone. 2-Chloroacetophenone in acetone (3.10 g, 200 ml) was added potassium thioacetate (2.80 g, 1.2 equivalents) and the reaction mixture was stirred overnight at RT. The salt precipitate was filtered off and the filtrate was concentrated. The residue was purified by flash chromatography on silica gel to give 2.04 g of α-thioacetyl acetophenone as orange reddish oil. $^1$H NMR (500 MHz, CHLOROFORM-D) δ ppm 7.98–8.02 (2 H, m) 7.60 (1 H, t, J=7.48 Hz) 7.48 (2 H, t, J=7.78 Hz) 4.40 (2 H, s) 2.41 (3 H, s). MS [ESI, MNa+] m/z calcd for C10H10O2SNa 217.04, found 217.16.

Intermediate 30

2-(3,5-bis(trifluoromethyl)benzylthio)-1-phenylethanone. α-Thioacetyl acetophenone was dissolved in methanol (1.00 g, 8 ml) and cooled to −10° C. Sodium methoxide in methanol (6.16 mmol, 1.2 equivalents, 1.4 ml) was added drop wise and the reaction mixture was stirred below 0° C. for 15 minutes. After cooling to −20° C., 3,5-bistrifluoromethylbenzylbromide (1.2 equivalents) was added; the reaction mixture was stirred for 1 hour below 0° C. and then was allowed to warm up to RT. It was then extracted with methylenechloride and washed with brine. After it was dried and concentrated, the residue was purified by flash chromatography on silica to give 1.34 g of 2-(3,5-bis(trifluoromethyl)benzylthio)-1-phenylethanone as a yellow oil. $^1$H NMR (500 MHz, MeOD) δ ppm 7.97 (3 H, s) 7.96 (1 H, d, J=1.22 Hz) 7.84 (1 H, s) 7.62 (1 H, t, J=7.48 Hz) 7.50 (2 H, t, J=7.63 Hz) 3.94 (2 H, s) 3.83 (2 H, s). MS [ESI, MNa+] m/z calcd for C17H12F6OSNa 401.05, found 401.08.

Intermediate 31

4-(3,5-bis(trifluoromethyl)benzylthio)-3-hydroxy-3-phenylbutanenitrile. 2-(3,5-bis(trifluoromethyl)benzylthio)-1-phenylethanone in anhydrous THF (230 mg, 0.4 ml) was added to a THF solution of lithium acetonitrilate (10 ml, 1.45 mmol, preformed by mixing n-butyllithium and acetonitrile in THF from −78° C. to −40° C.). The reaction mixture was then allowed to warm up to RT and then quenched by addition of aqueous ammonium chloride solution. After it was extracted with ethyl acetate, the organic layer was washed with brine and concentrated. The residue was purified by preparative HPLC to give 26 mg of 4-(3,5-bis(trifluoromethyl)benzylthio)-3-hydroxy-3-phenylbutanenitrile as a yellow oil. $^1$H NMR (500 MHz, MeOD) δ ppm 7.83 (3 H, s) 7.53 (2 H, d, J=7.63 Hz) 7.41 (2 H, t, J=7.63 Hz) 7.34 (1 H, t, J=7.32 Hz) 3.75 (1 H, d, J=13.73 Hz) 3.69 (1 H, d, J=13.43 Hz) 3.22 (1 H, d, J=16.79 Hz) 3.12 (1 H, d, J=16.48 Hz) 2.93–3.00 (2 H, m). MS [ESI, MNa+] m/z calcd for C19H15F6NOSNa 442.08, found 442.05.

Intermediate 32

N-(3,5-bis(trifluoromethyl)benzyl-2-oxo-2-phenylacetamide. Benzoylformic acid in acetone (3.00 g, 20 ml) was mixed with 3,5-bistrifluoromethylbenzylamine (tech. grade, 80%, 5.85 g, 1 equivalent) in benzene (20 ml). The resultant suspension was stirred at 0° C., and a suspension of DCC in benzene (4.34 g, 1.1 equivalents, 20 ml) was added slowly. The reaction mixture was allowed to warm up to RT and stirred overnight. The reaction mixture was quenched with brine and extracted with EtOAc. After concentration, the residue was purified by flash chromatography on silica gel to give 3.69 g of N-(3,5-bis(trifluoromethyl)benzyl-2-oxo-2-phenylacetamide as a yellow solid. $^1$H NMR (500 MHz, DMSO-D6) δ ppm 9.62 (1 H, t, J=5.80 Hz) 8.07 (2 H, s) 8.05 (1 H, s) 7.97–8.01 (2 H, m) 7.75 (1 H, t, J=7.32 Hz) 7.59 (2 H, t, J=7.93 Hz) 4.67 (2 H, d, J=6.10 Hz). MS [ESI, MH$^+$] m/z calcd for C17H12F6NO2 376.08, found 376.07.

Intermediate 33

N-(3,5-bis(trifluoromethyl)benzyl-3-cyano-2-hydroxy-2-phenylpropanamide. N-(3,5-bis(trifluoromethyl)benzyl-2-oxo-2-phenylacetamide was dissolved in anhydrous THF (246 mg, 5 ml) and cooled to 0° C. NaH (29 mg, 60% wt, 1.1 equivalents) was added and followed by addition of neat TMSCl (92 μl, 1.1 equivalent) while the reaction mixture turned greenish yellow immediately. After 10 minutes, the reaction mixture was cooled down to −78° C., and was added lithium acetonitrilate in THF (5.4 ml, 0.122 M, preformed by mixing n-butyllithium and acetonitrile in THF from −78° C. to −40° C.). The reaction mixture turned orange reddish immediately; it was then quenched with aqueous ammonium chloride solution and extracted with EtOAc. After it was dried and concentrated, the residue was purified by preparative HPLC to give 20 mg of N-(3,5-bis(trifluoromethyl)benzyl-3-cyano-2-hydroxy-2-phenylpropanamide as yellow oil. $^1$H NMR (500 MHz, MeOD) δ ppm 7.79 (1 H, s) 7.73 (2 H, s) 7.63 (2 H, d, J=7.63 Hz) 7.34–7.42 (3 H, m) 4.61 (1 H, d, J=15.56 Hz) 4.46 (1 H, d, J=15.87 Hz) 3.45 (1 H, d, J=17.09 Hz) 3.26 (1 H, d, J=16.48 Hz). MS [ESI, MH+] m/z calcd for C19H15F6N2O2 417.10, found 417.18.

Intermediate 34

1-(3,5-bis(trifluoromethyl)benzylamine-4-amino-2-phenylbutan-2-ol. N-(3,5-bis(trifluoromethyl)benzyl-3-cyano-2-hydroxy-2-phenylpropanamide (20 mg) was dissolved in neat borane dimethylsulfide complex (1.5 ml) and stirred at RT for 1 hour. The excess borane dimethylsulfide complex was removed under nitrogen stream and the residue was carefully quenched by slow addition of methanol. The methanol solution was heated to 70° C. for a while and was then purified by preparative HPLC to give 5.3 mg of 1-(3,5-bis(trifluoromethyl)benzylamine-4-amino-2-phenylbutan-2-ol TFA salt as clean oil. $^1$H NMR (500 MHz, MeOD) δ ppm 8.11 (3 H, s) 7.52–7.57 (2 H, m) 7.49 (2 H, t, J=7.63 Hz) 7.42 (1 H, t, J=7.17 Hz) 4.38 (1 H, d, J=13.73 Hz) 4.32 (1 H, d, J=13.43 Hz) 3.54 (1 H, d, J=12.82 Hz) 3.46 (1 H, d, J=12.82 Hz) 2.89–2.98 (1 H, m) 2.55 (1 H, ddd, J=12.51, 10.53, 5.04 Hz) 2.23–2.32 (2 H, m). HRMS [ESI, MH+] m/z calcd for C19H21F6N2O 407.1558, found 407.1568.

Intermediate 35

1-((2-phenylallyloxy)methyl)-3,5-bis(trifluoromethyl) benzene. To a suspension of methyltriphenylphosphonium bromide (2.96 g; 8.28 mmol) in tetrahydrofuran (90 mL) at 0° C. was added butyllithium (1.6 M in hexane, 5.2 mL, 8.3 mmol). The ice bath was removed, and stirring continued for 10 min. The resulting yellow solution was transferred slowly via canula to a solution of 2-(3,5-bis(trifluoromethyl)benzyloxy)-1-phenylethanone (2.0 g, 5.5 mmol) in THF (25 mL) at 0° C. After 1 h at 0° C., the ice bath was removed and stirring continued for 3 hours. The reaction was quenched by addition of saturated ammonium chloride and poured into pentane (150 mL). The mixture was washed with water (3×), then brine, dried over magnesium sulfate, and concentrated. Column chromatography (2.5%→25% ethyl acetate/hexanes) gave 1.51 g (76%). $^1$H NMR (500 MHz, CDCl$_3$) δ ppm 7.78 (s, 1H), 7.73 (s, 2H), 7.49 (m, 2H), 7.30–7.40 (m, 3H), 5.60 (s, 1H), 5.38 (d, J=1.2 Hz, 1H), 4.64 (s, 2H), 4.51 (s, 2H); $^{13}$C NMR (126 MHz, CDCl$_3$) δ ppm 144.1, 141.2, 138.5, 131.8 (q, J=33.6 Hz), 128.5, 128.1, 127.4 (d, J=2.9 Hz), 126.2, 123.4 (q, J=272.6 Hz), 121.5 (m), 115.2, 73.1, 70.3.

Intermediate 36

(R)-3-(3,5-bis(trifluoromethyl)benzyloxy)-2-phenylpropane-1,2-diol. A flask was charged with t-butyl alcohol (15 mL), water (15 mL), and AD-mix-β (4.20 g). The mixture was briefly stirred at room temperature, and then cooled to 0° C. To this was added 1-((2-phenylallyloxy)methyl)-3,5-bis(trifluoromethyl)benzene (1.0 g, 2.78 mmol) via syringe. After 2 h, the reaction was treated with osmium tetroxide (0.164 M in water, 0.15 mL) and stirring continued at 0° C. The reaction was allowed to slowly warm to room temperature in the dewar overnight. The reaction was quenched by addition of sodium thiosulfate (2.0 g in 10 mL water). The reaction was stirred for 20 min, and poured into ethyl acetate. The organics were washed with water (2×), then brine, dried over magnesium sulfate, and concentrated. Column chromatography (12%→50% ethyl acetate/hexanes) gave 1.01 g (93%) as a colorless oil. $^1$H NMR (500 MHz, CDCl$_3$) δ ppm 7.79 (s, 1H), 7.68 (s, 2H), 7.47 (m, 2H), 7.38 (m, 2H), 7.31 (m, 1H), 4.68 (d, J=13.1 Hz, 1H), 4.64 (d, J=12.8 Hz, 1H), 3.87–3.94 (m, 2H), 3.75–3.83 (m, 2H), 3.20 (s, 1H), 2.13 (t, J=6.4 Hz, 1H); $^{13}$C NMR (126 MHz, CDCl$_3$) δ ppm 141.5, 140.6, 132.0 (q, J=33.6 Hz), 128.6, 127.8, 127.4, 125.4, 123.4 (q, J=272.6 Hz), 121.8 (m), 76.4, 75.9, 72.3, 67.9; Mass spec.: 417.06 (MNa)$^+$.

Intermediate 37

(S)-3-(3,5-bis(trifluoromethyl)benzyloxy)-2-hydroxy-2-phenylpropyl pivalate. To a solution of (R)-3-(3,5-bis(trifluoromethyl)benzyloxy)-2-phenylpropane-1,2-diol (640 mg, 1.62 mmol) and pyridine (0.39 mL, 4.87 mmol) in dichloromethane (10 mL) at −78° C. was added trimethylacetylchloride (0.40 mL, 3.25 mmol), dropwise. The reaction was stirred at −78° C. for 30 min, and then allowed to gradually warm in the dewar to −60° C. The reaction was recooled to −78° C. and treated with saturated sodium bicarbonate (4 mL). The ice bath was removed, and the reaction allowed to warm to room temperature. The reaction was diluted with ether (30 mL), washed with water, then 1 M potassium bisulfate, then brine, dried over magnesium sulfate, and concentrated. Column chromatography (13%→25% ethyl acetate/hexanes) gave 640 mg (82%) as a colorless oil. $^1$H NMR (500 MHz, CDCl$_3$) δ ppm 7.79 (s, 1H), 7.69 (s, 2H), 7.48 (m, 2H), 7.36 (m, 2H), 7.30 (m, 1H), 4.65 (s, 2H), 4.47 (d, J=11.9 Hz, 1H), 4.40 (d, J=111.6 Hz, 1H), 3.80 (d, J=9.8 Hz, 1H), 3.75 (d, J=9.8 Hz, 1H), 3.12 (bs, 1H), 1.08 (s, 9H); $^{13}$C NMR (126 MHz, CDCl$_3$) δ ppm 178.6, 141.0, 140.7, 131.9 (q, J=33.6 Hz), 128.3, 127.8, 127.4 (m), 125.7, 123.4 (q, J=273.5 Hz), 121.7 (m), 75.8, 75.5, 72.3, 68.4, 38.9, 27.0; Mass spec.: 479.01 (MH)$^+$.

Intermediate 38

(S)-3-(3,5-bis(trifluoromethyl)benzyloxy)-2-phenyl-2-(triethylsilyloxy)propyl pivalate. To a solution of (S)-3-(3,5-bis(trifluoromethyl)benzyloxy)-2-hydroxy-2-phenylpropyl pivalate (310 mg, 0.65 mmol) in dichloromethane (7 mL) at −78° C. was added 2,6-lutidine (0.30 mL, 2.6 mmol) and triethylsilyl trifluoromethanesulfonate (0.44 mL, 1.94 mmol). The reaction was slowly warmed to 0° C. in the dewar. The reaction was recooled to −78° C., diluted with ether, and poured into water. The organics were washed with water, then 1 M potassium bisulfate, then water, then brine, dried over magnesium sulfate, and concentrated. Column chromatography (2.5%→4% ethyl acetate/hexanes) gave 380 mg (99%) as a colorless oil. $^1$H NMR (500 MHz, CDCl$_3$) δ ppm 7.79 (s, 1H), 7.71 (s, 2H), 7.46 (d, J=7.0 Hz, 2H), 7.33 (m, 2H), 7.27 (m, 1H), 4.61 (s, 2H), 4.56 (d, J=11.3 Hz, 1H), 4.28 (d, J=111.3 Hz, 1H), 3.80 (s, 2H), 1.08 (s, 9H), 0.91 (t, J=7.9 Hz, 9H), 0.58 (q, J=7.9 Hz, 6H); $^{13}$C NMR (126 MHz, CDCl$_3$) δ ppm 178.0, 142.3, 140.8, 131.8 (q, J=33.6 Hz), 128.1, 127.7, 127.4 (d, J=2.9 Hz), 126.2, 123.4 (q, J=273.5 Hz), 121.6 (m), 78.1, 76.0, 72.2, 68.1, 38.8, 27.1, 7.0, 6.6.

Intermediate 39

(R)-3-(3,5-bis(trifluoromethyl)benzyloxy)-2-phenyl-2-(triethylsilyloxy)propan-1-ol. To a solution of (S)-3-(3,5-bis(trifluoromethyl)benzyloxy)-2-phenyl-2-(triethylsilyloxy)propyl pivalate (380 mg, 0.64 mmol) in dichloromethane (10 mL) at −78° C. was added diisobutylaluminum hydride (1 M in dichloromethane) (1.92 mL, 1.92 mmol). The reaction was stirred for 20 min at −78° C., and quenched by the dropwise addition of methanol. The reaction was diluted with ether, and treated with saturated sodium potassium tartrate, and vigorously stirred for 48 hours. The organics were washed with water, then brine, dried over magnesium sulfate, and concentrated. Column chromatography (7.5% ethyl acetate/hexanes) gave 285 mg (87%) as a colorless oil. $^1$H NMR (500 MHz, CDCl$_3$) δ ppm 7.79 (s, 1H), 7.72 (s, 2H), 7.47 (m, 2H), 7.35 (m, 2H), 7.29 (m, 1H), 4.64 (s, 2H), 3.81–3.89 (m, 4H), 1.97 (t, J=6.4 Hz, 1H), 0.90 (t, J=7.9 Hz, 9H), 0.57 (q, J=7.9 Hz, 6H); $^{13}$C NMR (126 MHz, CDCl$_3$) δ ppm 142.2, 140.6, 131.6 (q, J=33.3 Hz), 128.1, 127.6, 127.2 (d, J=2.9 Hz), 126.1, 123.2 (q, J=272.7 Hz), 121.4 (m), 79.3, 75.3, 71.9, 68.1, 6.9, 6.4.

Intermediate 40

(S)-3-(3,5-bis(trifluoromethyl)benzyloxy)-2-phenyl-2-(triethylsilyloxy)propanal. To a solution of (R)-3-(3,5-bis(trifluoromethyl)benzyloxy)-2-phenyl-2-(triethylsilyloxy)propan-1-ol (285 mg, 0.56 mmol) in dichloromethane (3 mL) was added 3,3,3-triacetoxy-3-iodophthalide (285 mg, 0.67 mmol). The reaction was stirred at room temperature for 20 min, and quenched by the cautious addition of saturated sodium bicarbonate. The reaction was diluted with pentane and filtered to remove the insoluble precipitate. The organics were washed with saturated sodium bicarbonate, then water, then brine, dried over magnesium sulfate, and concentrated. Column chromatography (5%→10% ethyl acetate/hexanes) gave 250 mg (88%) as a colorless oil. $^1$H NMR (500 MHz, CDCl$_3$) δ ppm 9.64 (s, 1H), 7.83 (s, 1H), 7.76 (s, 2H), 7.49 (d, J=8.2 Hz, 2H), 7.40 (m, 2H), 7.34 (m, 1H), 7.49 (d, J=12.8 Hz, 1H), 4.65 (d, J=12.8 Hz, 1H), 4.16 (d, J=10.1 Hz, 1H), 3.82 (d, J=10.1 Hz, 1H), 1.00 (t, J=7.9 Hz, 9H), 0.72 (m, 6H); $^{13}$C NMR (126 MHz, CDCl$_3$) δ ppm 199.9, 140.5, 137.2, 131.8 (q, J=33.6 Hz), 128.7, 128.4, 127.5, 126.1, 123.4 (q, J=272.6 Hz), 121.7 (m), 84.7, 75.2, 72.3, 7.1, 6.6.

Intermediate 41

(S)-(1-(3,5-bis(trifluoromethyl)benzyloxy)-4-nitro-2-phenylbut-3-en-2-yloxy)triethylsilane. To a solution of (S)-3-(3,5-bis(trifluoromethyl)benzyloxy)-2-phenyl-2-(triethylsilyloxy)propanal (100 mg, 0.20 mmol) in nitromethane (0.4 mL) and t-butyl alcohol (0.4 mL) at room temperature was added lithium t-butoxide (2.0 mg). The resulting suspension was stirred at room temperature for 2 h. The reaction was diluted with ether, washed with water (2×), then brine, dried over magnesium sulfate, and concentrated. The crude residue (104 mg) was dissolved in dichloromethane (2 mL), cooled to 0° C., and treated with pyridine (96 μL, 1.2 mmol) and methanesulfonyl chloride (46 μL, 0.59 mmol). The ice bath was removed, and stirring continued for 30 min. The reaction was treated with triethylamine (0.14 mL, 0.99 mmol), and stirred 1 h. The reaction was diluted with pentane, washed with saturated sodium bicarbonate, then 1 M potassium bisulfate, then water, then brine, dried over magnesium sulfate, and concentrated. Column chromatography (5% ethyl acetate/hexanes) gave 60 mg (55%) as a colorless oil. $^1$H NMR (500 MHz, CDCl$_3$) δ ppm 7.81 (s, 1H), 7.70 (s, 2H), 7.47 (d, J=13.4 Hz, 1H), 7.32–7.43 (m, 5H), 7.29 (d, J=13.1 Hz, 1H), 4.69 (d, J=12.8 Hz, 1H), 4.65 (d, J=12.5 Hz, 1H), 3.96 (d, J=9.5 Hz, 1H), 3.85 (d, J=9.5 Hz, 1H), 0.88 (t, J=7.9 Hz, 9H), 0.52 (m, 6H); $^{13}$C NMR (126 MHz, CDCl$_3$) δ ppm 144.6, 140.3, 140.11, 140.05, 132.0 (q, J=33.6 Hz), 128.74, 128.71, 127.5 (d, J=2.9 Hz), 126.4, 123.3 (q, J=272.6 Hz), 122.0 (m), 77.3, 76.5, 72.3, 7.0, 6.5.

Intermediate 42

(S)-4-(3,5-bis(trifluoromethyl)benzyloxy)-3-phenyl-3-(triethylsilyloxy)butan-1-amine. A flask was charged with (S)-(1-(3,5-bis(trifluoromethyl)benzyloxy)-4-nitro-2-phenylbut-3-en-2-yloxy)triethylsilane (35 mg, 64 μmol), methanol (1.5 mL), and platinum dioxide (20 mg, 88 μmol). The flask was purged with hydrogen and stirred under a balloon of hydrogen for 2 h. The reaction was filtered through celite and concentrated. Column chromatography (5% methanol/dichloromethane) gave 20 mg (60%) as a colorless oil. Retention time: 1.98 min. (Phenomenex C18 3.0×50 mm, 10% MeOH/90% H$_2$O/0.1% TFA→90% MeOH/10% H$_2$O/0.1% TFA, Gradient time=2 min., Flow rate=5 mL/min.) Mass spec.: 522.16 (MH)$^+$.

EXAMPLE 1

1-(3,5-bis(trifluoromethyl)benzyloxy)-3-(dimethylamino)-2-phenylpropan-2-ol, trifluoroacetic acid salt. Excess amount of dimethylamine in methanol (2 M, 0.5 ml) was mixed with 2-((3,5-bis(trifluoromethyl)benzyloxy)methyl)-2-phenyloxirane (15 mg, 0.040 mmol). The reaction mixture was heated in microwave at 120° C. for 10 minutes. The cooled solution was concentrated, and the residue was purified by preparative HPLC to give the desired product as a TFA salt. $^1$H NMR (300 MHz, CHLOROFORM-D) δ ppm 7.79 (s, 1 H) 7.71 (s, 2 H) 7.53 (d, J=6.95 Hz, 2 H) 7.31–7.44 (m, 3 H) 4.66–4.76 (m, 1 H) 4.52–4.62 (m, 1 H) 3.90 (d, J=13.17 Hz, 1 H) 3.65 (s, 2 H) 3.44 (d, J=12.81 Hz, 1 H) 2.89 (s, 3 H) 2.57 (s, 3 H); LRMS [ESI, MH$^+$] m/z calcd for $C_{20}H_{22}NO_2F_6$ 422.16, found 422.09.

EXAMPLE 2

1-(3,5-bis(trifluoromethyl)benzyloxy)-3-amino-2-phenylpropan-2-ol, trifluoroacetic acid salt. Excess amount of ammonia in methanol (2 M, 0.5 ml) was mixed with 2-((3,5-bis(trifluoromethyl)benzyloxy)methyl)-2-phenyloxirane (15 mg, 0.040 mmol). The reaction mixture was heated in microwave at 120° C. for 10 minutes. The cooled solution was concentrated, and the residue was purified by preparative HPLC to give the desired product as a TFA salt. $^1$H NMR (300 MHz, CHLOROFORM-D) δ ppm 7.79 (s, 1 H) 7.70 (s, 2 H) 7.34 (s, 5 H) 4.64 (s, 2 H) 3.78 (s, 1 H) 3.64 (s, 2 H) 3.35 (s, 1 H); LRMS [ESI, MH$^+$] m/z calcd for $C_{18}H_{18}NO_2F_6$ 394.12, found 394.06.

EXAMPLE 3

1-(3,5-bis(trifluoromethyl)benzyloxy)-3-(methylamino)-2-phenylpropan-2-ol, trifluoroacetic acid salt. Excess amount of methylamine in methanol (2 M, 0.5 ml) was mixed with 2-((3,5-bis(trifluoromethyl)benzyloxy)methyl)-2-phenyloxirane (15 mg, 0.040 mmol). The reaction mixture was heated in microwave at 120° C. for 10 minutes. The cooled solution was concentrated, and the residue was purified by preparative HPLC to give the desired product as a TFA salt. $^1$H NMR (300 MHz, CHLOROFORM-D) δ ppm 7.81 (s, 1 H) 7.70 (s, 2 H) 7.30–7.43 (m, 5 H) 4.59–4.72 (m, 2 H) 3.73–3.86 (m, 1 H) 3.64 (d, J=9.88 Hz, 2 H) 3.36–3.49 (m, 1H) 2.68 (s, 3 H); LRMS [ESI, MH$^+$] m/z calcd for $C_{19}H_{20}NO_2F_6$ 408.14, found 408.08.

EXAMPLE 4

1-(3,5-bis(trifluoromethyl)benzyloxy)-4-amino-2-phenylbutan-2-ol, trifluoroacetic acid salt. Prepared as in General A, by using starting reagents (3,5-bis(trifluoromethyl)phenyl)methanol and phenylmagnesium chloride. $^1$H NMR (500 MHz, MeOD) δ ppm 7.88 (s, 3 H) 7.55 (dd, J=8.39, 1.37 Hz, 2 H) 7.41 (t, J=7.78 Hz, 2 H) 7.32 (t, J=7.32 Hz, 1 H) 4.68–4.75 (m, 2 H) 3.78–3.82 (m, 1 H) 3.72–3.77 (m, 1 H) 2.90–2.97 (m, 1 H) 2.81 (ddd, J=12.97, 7.78, 5.49 Hz, 1 H) 2.32–2.39 (m, 1 H) 2.23 (ddd, J=13.96, 8.16, 5.34 Hz, 1 H); $^{13}$C NMR (126 MHz, MeOD) δ ppm 143.32 (s) 142.20 (s) 131.69 (q, $J_{CCF}$=32.63 Hz) 128.46 (s) 127.76 (s) 127.48 (s) 125.61 (s) 123.85 (q, $J_{CF}$=271.59 Hz) 121.00–121.45 (m) 78.61 (s) 76.06 (s) 71.79 (s) 36.02 (s) 35.61 (s); HRMS [ESI, MH$^+$] m/z calcd for $C_{19}H_{20}NO_2F_6$ 408.1398, found 408.1382.

EXAMPLE 5

1-(3,5-bis(trifluoromethyl)benzyloxy)-4-(dimethylamino)-2-phenylbutan-2-ol, trifluoroacetic acid salt. 37 wt % formaldehyde solution in water (0.3 ml, 4 mmol), sodium acetate (140 mg, 1.7 mmol), acetic acid (0.06 ml, 1 mmol) and water (0.6 ml) were mixed together to form an aqueous solution. 1-(3,5-Bis(trifluoromethyl)benzyloxy)-4-amino-2-phenylbutan-2-ol TFA salt (30 mg, 0.058 mmol) in ether (0.3 ml) was then mixed with the above aqueous solution, followed by addition of sodium cyanoborohydride (30 mg, 0.48 mmol). The two layer slurry was stirred at room temperature for 20 minutes. The ether layer was separated from water layer and the water layer was further extracted twice by ether. The combined organic layer was concentrated, and the residue was purified by preparative HPLC to give the desired dimethyl tertiary amine as a TFA salt. $^1$H NMR (500 MHz, MeOH) δ ppm 7.86 (s, 3 H) 7.52 (d, J=8.24 Hz, 2 H) 7.39 (t, J=7.78 Hz, 2 H) 7.30 (t, J=7.32 Hz, 1 H) 4.66–4.73 (m, 2 H) 3.76–3.82 (m, 1 H) 3.72 (d, J=9.77 Hz, 1 H) 3.14 (ddd, J=13.05, 8.93, 6.71 Hz, 1 H) 2.91–2.98 (m, 1 H) 2.82 (d, J=11.60 Hz, 6 H) 2.43 (ddd, J=14.19, 8.85, 6.56 Hz, 1 H) 2.27 (ddd, J=14.11, 8.77, 5.49 Hz, 1 H); $^{13}$C NMR (126 MHz, MeOD) δ ppm 143.09 (s) 142.16 (s) 131.71 (q, $J_{CCF}$=33.59 Hz) 128.56 (s) 127.82 (s) 127.61 (s) 125.54 (s) 123.85 (q, $J_{CF}$=271.63 Hz) 121.27 (s) 78.50 (s) 75.69 (s) 71.80 (s) 54.76 (s) 43.10 (s) 42.22 (s) 32.95 (s); HRMS [ESI, MH$^+$] m/z calcd for $C_{21}H_{24}NO_2F_6$ 436.1711, found 436.1708.

EXAMPLE 6

1-(3,5-bis(trifluoromethyl)benzyloxy)-4-(methylamino)-2-phenylbutan-2-ol, trifluoroacetic acid salt. N-(4-(3,5-bis(trifluoromethyl)benzyloxy)-3-hydroxy-3-phenylbutyl)-2,2,2-trifluoro-N-methylacetamide (7.5 mg, 0.015 mmol) was dissolved in excess ammonia in methanol (2 M, 2 ml) and stirred at room temperature for 1 hour. The solution was concentrated, and the residue was purified by preparative HPLC and to give mono-methyl amine as a TFA salt. $^1$H NMR (500 MHz, MeOH) δ ppm 7.69 (s, 2H) 7.68 (s, 1H) 7.31–7.38 (m, 2 H) 7.19–7.25 (m, 2 H) 7.14 (t, J=6.71 Hz, 1 H) 4.49–4.56 (m, 2 H) 3.60–3.64 (m, 1 H) 3.53–3.57 (m, 1 H) 2.77–2.84 (m, 1 H) 2.66–2.74 (m, 1 H) 2.42–2.47 (m, 3 H) 2.16–2.24 (m, 1 H) 2.06 (ddd, J=13.89, 7.93, 5.65 Hz, 1 H); $^{13}$C NMR (126 MHz, MeOH) δ ppm 144.34 (s) 143.23 (s) 132.78 (q, $J_{CCF}$=33.94 Hz) 129.56 (s) 128.83 (s) 128.61 (s) 126.65 (s) 124.90 (q, $J_{CF}$=271.28 Hz) 122.31 (s) 79.55 (s) 77.00 (s) 72.87 (s) 46.94 (s) 35.46 (s) 33.81 (s); HRMS [ESI, MH$^+$] m/z calcd for $C_{20}H_{22}NO_2F_6$ 422.1555, found 422.1552.

Examples 7 and 8 are Separate Isomers of a Racemic Mixture

EXAMPLE 7

1-(3,5-bis(trifluoromethyl)benzyloxy)-4-amino-2-phenylbutan-2-ol, trifluoroacetic acid salt. Prepared by separating and isolating racemic 1-(3,5-bis(trifluoromethyl)benzyloxy)-4-amino-2-phenylbutan-2-ol, trifluoroacetic acid salt by chiral preparative HPLC using chiralcel OD column.

EXAMPLE 8

1-(3,5-bis(trifluoromethyl)benzyloxy)-4-amino-2-phenylbutan-2-ol, trifluoroacetic acid salt. Prepared by separating and isolating racemic 1-(3,5-bis(trifluoromethyl)benzyloxy)-4-amino-2-phenylbutan-2-ol, trifluoroacetic acid salt by chiral HPLC system using chiralcel OD column.

Example 8 was also prepared using a chiral synthetic procedure.

(S)-1-(3,5-bis(trifluoromethyl)benzyloxy)-4-amino-2-phenylbutan-2-ol. To a solution of (S)-4-(3,5-bis(trifluoromethyl)benzyloxy)-3-phenyl-3-(triethylsilyloxy)butan-1-amine (20 mg, 38 μmol) in tetrahydrofuran (1 mL) was added tetrabutylammonium fluoride (1 M in tetrahydrofuran, 77 μL, 77 μmol). The reaction was stirred for 20 min, diluted with an equal volume of methanol, loaded onto a strong cation exchange cartridge, and flushed with methanol. The product was eluted with 2 M ammonia in methanol and concentrated. The product was purified by preparative HPLC (trifluoroacetic acid/methanol/water) to give 10.1 mg (51%) as the trifluoroacetic acid salt. $[\alpha]^{20}_D=-9.38$ (c=1.0, MeOH); $^1$H NMR (500 MHz, MeOD) δ ppm 7.88 (s, 3 H) 7.55 (dd, J=8.39, 1.37 Hz, 2 H) 7.41 (t, J=7.78 Hz, 2 H) 7.32 (t, J=7.32 Hz, 1 H) 4.68–4.75 (m, 2 H) 3.78–3.82 (m, 1 H) 3.72–3.77 (m, 1 H) 2.90–2.97 (m, 1 H) 2.81 (ddd, J=12.97, 7.78, 5.49 Hz, 1 H) 2.32–2.39 (m, 1 H) 2.23 (ddd, J=13.96, 8.16, 5.34 Hz, 1 H); $^{13}$C NMR (126 MHz, MeOD) δ ppm 143.32 (s) 142.20 (s) 131.69 (q, $J_{CCF}$=32.63 Hz) 128.46 (s) 127.76 (s) 127.48 (s) 125.61 (s) 123.85 (q, $J_{CF}$=271.59 Hz) 121.00–121.45 (m) 78.61 (s) 76.06 (s) 71.79 (s) 36.02 (s) 35.61 (s); HRMS [ESI, MH$^+$] m/z calcd for $C_{19}H_{20}NO_2F_6$ 408.1398, found 408.1382.

EXAMPLE 9

1-(3,5-bis(trifluoromethyl)benzyloxy)-4-amino-2-p-tolylbutan-2-ol, trifluoroacetic acid salt. Prepared as in General A, by using starting reagents (3,5-bis(trifluoromethyl)phenyl)methanol and p-tolylmagnesium bromide. $^1$H NMR (500 MHz, MeOD) δ ppm 7.88 (s, 1 H) 7.86 (s, 2 H) 7.41 (d, J=7.93 Hz, 2 H) 7.22 (d, J=7.93 Hz, 2 H) 4.67–4.74 (m, 2 H) 3.76–3.79 (m, 1 H) 3.69–3.73 (m, 1 H) 2.92 (ddd, J=12.82, 7.78, 7.48 Hz, 1 H) 2.81 (ddd, J=12.82, 7.63, 5.49 Hz, 1 H) 2.36 (s, 3 H) 2.30–2.35 (m, 1 H) 2.20 (ddd, J=13.89, 8.24, 5.34 Hz, 1 H); $^{13}$C NMR (126 MHz, MeOD) δ ppm 142.23 (s) 140.21 (s) 137.27 (s) 131.66 (q, $J_{CCF}$=33.27 Hz) 129.06 (s) 127.72 (s) 125.53 (s) 123.84 (q, $J_{CF}$=272.55 Hz) 121.19 (s) 78.68 (s) 76.01 (s) 71.74 (s) 36.04 (s) 35.54 (s) 19.99 (s); HRMS [ESI, MH$^+$] m/z calcd for $C_{20}H_{22}NO_2F_6$ 422.1555, found 422.1562.

EXAMPLE 10

1-(3,5-bis(trifluoromethyl)benzyloxy)-4-amino-2-(3,4-dichlorophenyl)butan-2-ol, trifluoroacetic acid salt. Prepared as in General A, by using starting reagents (3,5-bis(trifluoromethyl)phenyl)methanol and 3,4-dichlorophenylmagnesium bromide. $^1$H NMR (500 MHz, MeOD) δ ppm 7.89 (s, 1 H) 7.86 (s, 2 H) 7.75 (d, J=2.14 Hz, 1 H) 7.55 (d, J=8.24 Hz, 1 H) 7.44 (dd, J=8.24, 2.14 Hz, 1 H) 4.65–4.78 (m, 2 H) 3.67–3.79 (m, 2 H) 2.88–3.00 (m, 1 H) 2.75–2.85 (m, 1 H) 2.25–2.36 (m, 1 H) 2.13–2.24 (m, 1 H); HRMS [ESI, MH$^+$] m/z calcd for $C_{19}H_{18}NO_2F_6Cl_2$ 476.0619, found 476.0606.

EXAMPLE 11

1-(3,5-bis(trifluoromethyl)benzyloxy)-4-amino-2-(naphthalen-2-yl)butan-2-ol, trifluoroacetic acid salt. Prepared as in General A, by using starting reagents (3,5-bis(trifluoromethyl)phenyl)methanol and 2-naphthylmagnesium bromide. $^1$H NMR (500 MHz, MeOD) δ ppm 8.08 (s, 1 H) 7.86–7.92 (m, 6 H) 7.62 (dd, J=8.55, 1.83 Hz, 1 H) 7.49–7.54 (m, 2 H) 4.70–4.76 (m, 2 H) 3.89–3.93 (m, 1 H) 3.84–3.87 (m, 1 H) 2.96 (dt, J=12.89, 7.59 Hz, 1 H) 2.82 (ddd, J=13.05, 7.71, 5.80 Hz, 1 H) 2.40–2.46 (m, 1 H) 2.35 (ddd, J=14.04, 8.24, 5.49 Hz, 1 H); $^{13}$C NMR (126 MHz, MeOD) δ ppm 142.16 (s) 140.66 (s) 133.65 (s) 133.13 (s) 131.67 (q, $J_{CCF}$=32.63 Hz) 128.21 (s) 128.12 (s) 127.74 (s) 127.56 (s) 126.36 (s) 126.21 (s) 124.85 (s) 123.48 (s) 123.80 (q, $J_{CF}$=271.59 Hz) 121.21 (s) 78.53 (s) 76.27 (s) 71.83 (s) 36.07 (s) 35.47 (s); HRMS [ESI, MH$^+$] m/z calcd for $C_{23}H_{22}NO_2F_6$ 458.1555, found 458.1577.

EXAMPLE 12

1-(3,5-bis(trifluoromethyl)benzyloxy)-4-amino-2-(3-fluorophenyl)butan-2-ol, trifluoroacetic acid salt. Prepared as in General A, by using starting reagents (3,5-bis(trifluoromethyl)phenyl)methanol and 3-fluorophenylmagnesium bromide. $^1$H NMR (500 MHz, MeOD) δ ppm 7.89 (s, 1 H) 7.87 (s, 2 H) 7.42 (td, J=8.01, 6.26 Hz, 1 H) 7.31–7.37 (m, 2 H) 7.06 (td, J=8.70, 1.83 Hz, 1 H) 4.68–4.76 (m, 2 H) 3.7–3.81 (m, 2 H) 3.32–3.34 (m, 4 H) 2.90–2.97 (m, 1 H) 2.80 (ddd, J=12.97, 7.63, 5.65 Hz, 1 H) 2.30–2.37 (m, 1 H) 2.21 (ddd, J=14.04, 8.24, 5.49 Hz, 1 H); HRMS [ESI, MH$^+$] m/z calcd for $C_{19}H_{19}NO_2F_7$ 426.1304, found 426.1323.

EXAMPLE 13

1-(3,5-bis(trifluoromethyl)benzyloxy)-4-amino-2-(4-fluoro-3-methylphenyl)butan-2-ol, trifluoroacetic acid salt. Prepared as in General A, by using starting reagents (3,5-bis(trifluoromethyl)phenyl)methanol and 4-fluoro-3-methylphenylmagnesium bromide. $^1$H NMR (500 MHz, MeOD) δ ppm 7.89 (s, 1 H) 7.87 (s, 2 H) 7.41 (dd, J=7.17, 2.29 Hz, 1 H) 7.32–7.37 (m, 1 H) 7.05 (t, J=9.16 Hz, 1 H) 4.68–4.75 (m, 2 H) 3.69–3.79 (m, 2 H) 2.88–2.96 (m, 1 H) 2.81 (ddd, J=12.89, 7.71, 5.65 Hz, 1 H) 2.29 (s, 3 H) 2.28–2.35 (m, 1 H) 2.20 (ddd, J=13.89, 8.09, 5.49 Hz, 1 H); HRMS [ESI, MH$^+$] m/z calcd for $C_{20}H_{21}NO_2F_7$ 440.1461, found 440.1477.

EXAMPLE 14

1-(3,5-bis(trifluoromethyl)benzyloxy)-4-amino-2-(3-methoxyphenyl)butan-2-ol, trifluoroacetic acid salt. Prepared as in General A, by using starting reagents (3,5-bis(trifluoromethyl)phenyl)methanol and 3-methoxyphenylmagnesium bromide. $^1$H NMR (500 MHz, MeOD) δ ppm 7.89 (s, 3 H) 7.32 (t, J=7.93 Hz, 1 H) 7.13–7.15 (m, 1 H) 7.07 (ddd, J=7.78, 0.92, 0.76 Hz, 1 H) 6.89 (dd, J=8.24, 2.44 Hz, 1 H) 4.68–4.75 (m, 2 H) 3.82 (s, 3 H) 3.71–3.81 (m, 2 H) 2.93 (ddd, J=13.05, 7.63, 7.40 Hz, 1 H) 2.81 (ddd, J=12.89, 7.71, 5.65 Hz, 1 H) 2.29–2.36 (m, 1 H) 2.21 (ddd, J=13.96, 8.16, 5.34 Hz, 1 H); $^{13}$C NMR (126 MHz, MeOD) δ ppm 160.40 (s) 145.03 (s) 142.19 (s) 131.69 (q, $J_{CCF}$=32.70 Hz) 129.54 (s) 127.75 (s) 123.84 (q, $J_{CF}$=271.66 Hz) 121.26 (s) 117.71 (s) 112.42 (s) 111.97 (s) 78.58 (s) 76.07 (s) 71.79 (s) 54.64 (s) 36.03 (s) 35.59 (s); HRMS [ESI, MH$^+$] m/z calcd for $C_{20}H_{22}NO_3F_6$ 438.1504, found 438.1502.

EXAMPLE 15

1-(3,5-bis(trifluoromethyl)benzyloxy)-4-amino-2-(3,4-difluorophenyl)butan-2-ol, trifluoroacetic acid salt. Prepared as in General A, by using starting reagents (3,5-bis(trifluoromethyl)phenyl)methanol and 3,4-difluorophenylmagnesium bromide. $^1$H NMR (500 MHz, MeOD) δ ppm 7.89 (s, 1 H) 7.86 (s, 2 H) 7.39–7.52 (m, 1 H) 7.20–7.38 (m, 2 H) 4.62–4.78 (m, 2 H) 3.65–3.79 (m, 2 H) 2.87–2.99 (m, 1 H) 2.74–2.87 (m, 1 H) 2.24–2.38 (m, 1 H) 2.11–2.25 (m, 1 H); HRMS [ESI, MH$^+$] m/z calcd for $C_{19}H_{18}NO_2F_8$ 444.1210, found 444.1214.

EXAMPLE 16

1-(3,5-bis(trifluoromethyl)benzyloxy)-4-amino-2-(4-(dimethylamino)phenyl)butan-2-ol, trifluoroacetic acid salt. Prepared as in General A, by using starting reagents (3,5-bis(trifluoromethyl)phenyl)methanol and 4-(N,N)dimethylaminophenylmagnesium bromide. $^1$H NMR (500 MHz, MeOD) δ ppm 7.89 (s, 1 H) 7.87 (s, 2 H) 7.70–7.77 (m, 2 H) 7.57 (d, J=8.85 Hz, 2 H) 4.68–4.76 (m, 2 H) 3.77 (s, 2 H) 3.27 (s, 6 H) 2.96 (dt, J=12.89, 7.59 Hz, 1 H) 2.77–2.85 (m, 1 H) 2.30–2.38 (m, 1 H) 2.24 (ddd, J=14.11, 8.47, 5.49 Hz, 1 H); LRMS [ESI, MH$^+$] m/z calcd for $C_{21}H_{25}N_2O_2F_6$ 451.18, found 451.15.

EXAMPLE 17

1-(3,5-bis(trifluoromethyl)benzyloxy)-4-amino-2-m-tolylbutan-2-ol, trifluoroacetic acid salt. Prepared as in General A, by using starting reagents (3,5-bis(trifluoromethyl)phenyl)methanol and 3-methylphenylmagnesium chloride. $^1$H NMR (500 MHz, MeOD) δ ppm 7.88 (s, 3 H) 7.37 (s, 1 H) 7.27–7.33 (m, 2 H) 7.14 (d, J=7.02 Hz, 1 H) 4.67–4.74 (m, 2 H) 3.71–3.81 (m, 2 H) 2.92 (ddd, J=12.97, 7.63, 7.48 Hz, 1 H) 2.80 (ddd, J=12.97, 7.78, 5.49 Hz, 1 H) 2.38 (s, 3 H) 2.30–2.37 (m, 1 H) 2.21 (ddd, J=13.96, 8.16, 5.34 Hz, 1 H); $^{13}$C NMR (126 MHz, MeOD) δ ppm 143.22 (s) 142.22 (s) 138.23 (s) 131.63 (q, $J_{CCF}$=33.96 Hz) 128.38 (s) 128.12 (s) 127.72 (s) 126.21 (s) 123.83 (q, $J_{CF}$=271.66 Hz) 122.64 (s) 121.20 (s) 78.67 (s) 76.06 (s) 71.77 (s) 36.05 (s) 35.56 (s) 20.64 (s); HRMS [ESI, MH$^+$] m/z calcd for $C_{20}H_{22}NO_2F_6$ 422.1555, found 422.1555.

EXAMPLE 18

1-(3,5-bis(trifluoromethyl)benzyloxy)-4-amino-2-(3,5-dimethylphenyl)butan-2-ol, trifluoroacetic acid salt. Prepared as in General A, by using starting reagents (3,5-bis(trifluoromethyl)phenyl)methanol and 3,5-dimethylphenylmagnesium bromide. $^1$H NMR (500 MHz, MeOD) δ ppm 7.88 (s, 3 H) 7.14 (s, 2 H) 6.97 (s, 1 H) 4.66–4.74 (m, 2 H) 3.68–3.80 (m, 2 H) 2.92 (ddd, J=12.74, 7.78, 7.55 Hz, 1H) 2.75–2.84 (m, 1 H) 2.33 (s, 6 H) 2.28–2.35 (m, 1 H) 2.20 (ddd, J=13.89, 8.24, 5.34 Hz, 1 H); $^{13}$C NMR (126 MHz, MeOD) δ ppm 143.13 (s) 142.26 (s) 138.11 (s) 131.68 (q, $J_{CCF}$=32.70 Hz) 128.89 (s) 127.70 (s) 123.85 (q, $J_{CF}$=271.66 Hz) 123.32 (s) 121.19 (s) 78.75 (s) 76.06 (s) 71.76 (s) 36.08 (s) 35.53 (s) 20.54 (s); HRMS [ESI, MH$^+$] m/z calcd for $C_{21}H_{24}NO_2F_6$ 436.1711, found 436.1719.

EXAMPLE 19

1-(3,5-bis(trifluoromethyl)benzyloxy)-4-amino-2-(3,5-difluorophenyl)butan-2-ol, trifluoroacetic acid salt. Prepared as in General A, by using starting reagents (3,5-bis(trifluoromethyl)phenyl)methanol and 3,5-difluorophenylmagnesium bromide. $^1$H NMR (500 MHz, MeOD) δ ppm 7.89 (s, 1 H) 7.87 (s, 2 H) 7.14–7.20 (m, 2 H) 6.87–6.93 (m, J=8.93, 8.93, 2.44, 2.29 Hz, 1 H) 4.68–4.76 (m, 2 H) 3.72–3.78 (m, 2 H) 2.95 (dt, J=12.89, 7.59 Hz, 1 H) 2.77–2.84 (m, 1 H) 2.26–2.34 (m, 1 H) 2.19 (ddd, J=13.96, 8.32, 5.49 Hz, 1 H); HRMS [ESI, MH$^+$] m/z calcd for $C_{19}H_{18}NO_2F_8$ 444.1210, found 444.1227.

EXAMPLE 20

1-(3,5-bis(trifluoromethyl)benzyloxy)-4-amino-2-(4-methoxyphenyl)butan-2-ol, trifluoroacetic acid salt. Prepared as in General A, by using starting reagents (3,5-bis(trifluoromethyl)phenyl)methanol and 4-anisylmagnesium bromide. $^1$H NMR (500 MHz, MeOD) δ ppm 7.88 (s, 3 H) 7.40–7.46 (m, 2 H) 6.91–6.97 (m, 2 H) 4.67–4.74 (m, 2 H) 3.82 (s, 3 H) 3.73 (dd, J=33.88, 9.46 Hz, 2 H) 2.93 (ddd, J=12.97, 7.63, 7.48 Hz, 1 H) 2.82 (ddd, J=12.67, 7.63, 5.34 Hz, 1 H) 2.33 (dt, J=14.11, 7.74 Hz, 1 H) 2.20 (ddd, J=13.96, 8.32, 5.49 Hz, 1 H); $^{13}$C NMR (126 MHz, MeOD) δ ppm 142.24 (s) 135.09 (s) 131.57 (q, $J_{CCF}$=33.96 Hz) 127.75 (s) 127.73 (s) 126.80 (s) 123.86 (q, $J_{CF}$=271.66 Hz) 121.21 (s) 113.76 (s) 78.70 (s) 75.80 (s) 71.74 (s) 54.69 (s) 36.06 (s) 35.58 (s); HRMS [ESI, MH$^+$] m/z calcd for $C_{20}H_{22}NO_3F_6$ 438.1504, found 438.1524.

EXAMPLE 21

1-(3,5-bis(trifluoromethyl)benzyloxy)-4-amino-2-(3-chlorophenyl)butan-2-ol, trifluoroacetic acid salt. Prepared as in General A, by using starting reagents (3,5-bis(trifluoromethyl)phenyl)methanol and 3-chlorophenylmagnesium bromide. $^1$H NMR (500 MHz, MeOD) δ ppm 7.89 (s, 1 H) 7.88 (s, 2 H) 7.62 (t, J=1.83 Hz, 1 H) 7.43–7.47 (m, 1 H) 7.39 (t, J=7.93 Hz, 1 H) 7.32–7.35 (m, 1 H) 4.68–4.75 (m, 2 H) 3.73–3.80 (m, 2 H) 2.91–2.98 (m, 2 H) 2.80 (ddd, J=12.97, 7.93, 5.65 Hz, 1 H) 2.29–2.37 (m, 1 H) 2.21 (ddd, J=13.96, 8.32, 5.49 Hz, 1 H); $^{13}$C NMR (126 MHz, MeOD) δ ppm 146.09 (s) 142.04 (s) 134.60 (s) 131.68 (q, $J_{CCF}$=33.96 Hz) 129.95 (s) 127.82 (s) 127.53 (s) 126.10 (s) 124.05 (s) 123.82 (q, $J_{CF}$271.66 Hz) 121.29 (s) 78.20 (s) 75.70 (s) 71.77 (s) 35.88 (s) 35.60 (s); HRMS [ESI, MH$^+$] m/z calcd for $C_{19}H_{19}NO_2F_6Cl$ 442.1009, found 442.1014.

EXAMPLE 22

1-(3,5-bis(trifluoromethyl)benzyloxy)-4-amino-2-(4-methylnaphthalen-1-yl)butan-2-ol, trifluoroacetic acid salt. Prepared as in General A, by using starting reagents (3,5-bis(trifluoromethyl)phenyl)methanol and 4-methyl-1-naphthylmagnesium bromide. $^1$H NMR (500 MHz, MeOD) δ ppm 8.58 (d, J=8.24 Hz, 1 H) 8.11 (dd, J=8.39, 1.37 Hz, 1 H) 7.84 (s, 1 H) 7.79 (s, 2 H) 7.72 (d, J=7.63 Hz, 1 H) 7.47–7.56 (m, 2 H) 7.36 (d, J=7.63 Hz, 1 H) 4.64–4.73 (m, 2 H) 4.11–4.21 (m, 2 H) 2.93 (t, J=7.17 Hz, 2 H) 2.70 (s, 3 H) 2.69–2.77 (m, 1 H) 2.53 (dt, J=14.34, 7.63 Hz, 1 H); $^{13}$C NMR (126 MHz, MeOD) δ ppm 142.03 (s) 136.36 (s) 135.26 (s) 134.20 (s) 131.65 (q, $J_{CCF}$=32.70 Hz) 131.02 (s) 127.82 (s) 127.80 (s) 126.05 (s) 125.84 (s) 125.34 (s) 125.25 (s) 125.16 (s) 123.66 (q, $J_{CF}$=271.66 Hz) 121.21 (s) 77.28 (s) 77.13 (s) 71.70 (s) 36.32 (s) 35.19 (s) 18.76 (s); HRMS [ESI, MH$^+$] m/z calcd for $C_{24}H_{24}NO_2F_6$ 472.1711, found 472.1718.

EXAMPLE 23

1-(3,5-bis(trifluoromethyl)benzyloxy)-4-amino-2-(3-fluoro-4-methoxyphenyl)butan-2-ol, trifluoroacetic acid salt. Prepared as in General A, by using starting reagents (3,5-bis(trifluoromethyl)phenyl)methanol and 3-fluoro-4-methoxyphenylmagnesium bromide. $^1$H NMR (500 MHz, MeOD) δ ppm 7.89 (s, 1 H) 7.87 (s, 2 H) 7.31 (dd, J=12.97, 2.29 Hz, 1 H) 7.22–7.26 (m, 1H) 7.11 (t, J=8.70 Hz, 1 H) 4.67–4.75 (m, 2 H) 3.90 (s, 3 H) 3.67–3.76 (m, 2 H) 2.88–2.97 (m, 1 H) 2.77–2.85 (m, 1 H) 2.31 (dt, J=14.11, 7.74 Hz, 1 H) 2.18 (ddd, J=13.96, 8.16, 5.34 Hz, 1 H); HRMS [ESI, MH$^+$] m/z calcd for $C_{20}H_{21}NO_3F_7$ 456.1410, found 456.1416.

EXAMPLE 24

1-(3,5-bis(trifluoromethyl)benzyloxy)-4-amino-2-(3-chloro-5-fluorophenyl)butan-2-ol, trifluoroacetic acid salt. Prepared as in General A, by using starting reagents (3,5-bis(trifluoromethyl)phenyl)methanol and 3-chloro-5-fluorophenylmagnesium bromide. $^1$H NMR (500 MHz, MeOD) δ ppm 7.89 (s, 1 H) 7.87 (s, 2 H) 7.43 (s, 1 H) 7.28 (dd, J=10.07, 1.53 Hz, 1 H) 7.17 (dt, J=8.24, 1.83 Hz, 1 H) 4.68–4.76 (m, 2 H) 3.76 (s, 2 H) 2.95 (ddd, J=12.97, 7.63, 7.48 Hz, 1 H) 2.77–2.86 (m, 1 H) 2.26–2.34 (m, 1 H) 2.19 (ddd, J=14.04, 8.24, 5.49 Hz, 1 H); $^{13}$C NMR (126 MHz, MeOD) δ ppm 157.02 (d, $J_{CF}$=1246.38 Hz) 148.57 (s) 141.93 (s) 135.27 (s) 131.50 (q, $J_{CCF}$=33.96 Hz) 127.64 (s) 123.90 (q, $J_{CF}$=271.67 Hz) 122.18 (s) 121.33 (s) 114.81 (d, $J_{CCF}$=26.41 Hz) 111.70 (d, $J_{CCF}$=22.64 Hz) 77.83 (s) 75.60 (s) 71.75 (s) 35.76 (s) 35.56 (s); HRMS [ESI, MH$^+$] m/z calcd for $C_{19}H_{18}NO_2F_7Cl$ 460.0914, found 460.0936.

EXAMPLE 25

1-(3,5-bis(trifluoromethyl)benzyloxy)-4-amino-2-(5-fluoro-2-methoxyphenyl)butan-2-ol, trifluoroacetic acid salt. Prepared as in General A, by using starting reagents (3,5-bis(trifluoromethyl)phenyl)methanol and 5-fluoro-2-methoxyphenylmagnesium bromide. $^1$H NMR (500 MHz, MeOD) δ ppm 7.87 (s, 1 H) 7.82 (s, 2 H) 7.45 (dd, J=10.22, 3.20 Hz, 1 H) 7.05 (ddd, J=8.85, 7.63, 3.05 Hz, 1 H) 6.97–7.01 (m, 1 H) 4.60–4.76 (m, 2 H) 3.91–4.00 (m, 2 H) 3.77 (s, 3 H) 2.82–2.91 (m, 1 H) 2.71–2.78 (m, 1 H) 2.52–2.59 (m, 1 H) 2.20 (dt, J=14.04, 7.63 Hz, 1 H); HRMS [ESI, MH$^+$] m/z calcd for $C_{20}H_{21}NO_3F_7$ 456.1410, found 456.1405.

EXAMPLE 26

1-(3,5-bis(trifluoromethyl)benzyloxy)-4-amino-2-(2,3-dimethylphenyl)butan-2-ol, trifluoroacetic acid salt. Prepared as in General A, by using starting reagents (3,5-bis(trifluoromethyl)phenyl)methanol and 2,3-dimethylphenylmagnesium bromide. $^1$H NMR (500 MHz, MeOD) δ ppm 7.88 (s, 3 H) 7.43 (s, 1 H) 7.07 (d, 1 H) 6.97–7.04 (m, 1 H) 4.68–4.77 (m, 2 H) 3.84–3.92 (m, 2 H) 2.87–2.97 (m, 2 H) 2.45 (s, 3 H) 2.38–2.46 (m, 1 H) 2.32 (s, 3 H) 2.29 (ddd, J=14.19, 7.93, 5.95 Hz, 1 H); $^{13}$C NMR (126 MHz, MeOD) δ ppm 142.20 (s) 140.21 (s) 135.46 (s) 132.95 (s) 132.20 (s) 131.31 (q, $J_{CF}$=33.96 Hz) 128.30 (s) 127.94 (s) 127.79 (s) 123.80 (q, $J_{CF}$=271.66 Hz) 121.23 (s) 77.08 (s) 77.00 (s) 71.65 (s) 36.24 (s) 34.50 (s) 21.22 (s) 20.19 (s); HRMS [ESI, MH$^+$] m/z calcd for $C_{21}H_{24}NO_2F_6$ 436.1711, found 436.1718.

EXAMPLE 27

1-(3,5-bis(trifluoromethyl)benzyloxy)-4-amino-2-(2,5-dimethoxyphenyl)butan-2-ol, trifluoroacetic acid salt. Prepared as in General A, by using starting reagents (3,5-bis(trifluoromethyl)phenyl)methanol and 2,5-dimethoxyphenylmagnesium bromide. $^1$H NMR (500 MHz, MeOD) δ ppm 7.87 (s, 1 H) 7.82 (s, 2 H) 7.29 (d, J=3.05 Hz, 1 H) 6.91–6.97 (m, 1 H) 6.84–6.91 (m, 1 H) 4.58–4.74 (m, 2 H) 3.95 (s, 2 H) 3.79 (s, 3 H) 3.74 (s, 3 H) 2.83–2.91 (m, 1 H) 2.68–2.81 (m, 1 H) 2.53–2.62 (m, 1 H) 2.14–2.24 (m, 1 H); HRMS [ESI, MH$^+$] m/z calcd for $C_{21}H_{24}NO_4F_6$ 468.1610, found 468.1602.

EXAMPLE 28

1-(3,5-bis(trifluoromethyl)benzyloxy)-4-amino-2-(4-methoxy-2-methylphenyl)butan-2-ol, trifluoroacetic acid salt. Prepared as in General A, by using starting reagents (3,5-bis(trifluoromethyl)phenyl)methanol and 4-methoxy-2-methylphenylmagnesium bromide. $^1$H NMR (500 MHz, MeOD) δ ppm 7.89 (s, 3 H) 7.48 (d, J=8.55 Hz, 1 H) 6.73–6.79 (m, 2 H) 4.69–4.77 (m, 2 H) 3.82–3.89 (m, 2 H) 3.79 (s, 3 H) 2.88–2.97 (m, 2 H) 2.48 (s, 3 H) 2.34–2.44 (m, 1 H) 2.23–2.34 (m, 1 H); HRMS [ESI, MH$^+$] m/z calcd for $C_{21}H_{24}NO_3F_6$ 452.1660, found 452.1667.

EXAMPLE 29

1-(3,5-bis(trifluoromethyl)benzyloxy)-4-amino-2-(5-fluoro-2-methylphenyl)butan-2-ol, trifluoroacetic acid salt. Prepared as in General A, by using starting reagents (3,5-bis(trifluoromethyl)phenyl)methanol and 5-fluoro-2-methylphenylmagnesium bromide. $^1$H NMR (500 MHz, MeOD) δ ppm 7.88 (s, 1 H) 7.87 (s, 2 H) 7.42 (dd, J=11.60, 2.75 Hz, 1 H) 7.19 (dd, J=8.09, 6.26 Hz, 1 H) 6.94 (td, J=8.09, 2.75 Hz, 1 H) 4.69–4.78 (m, 2 H) 3.88–3.95 (m, 2 H) 2.93–3.00 (m, 1 H) 2.84–2.90 (m, 1 H) 2.45 (s, 3 H) 2.40 (ddd, J=14.34, 8.55, 5.80 Hz, 1 H) 2.25–2.33 (m, 1 H); HRMS [ESI, MH$^+$] m/z calcd for $C_{20}H_{21}NO_2F_7$ 440.1461, found 440.1467.

EXAMPLE 30

1-(3,5-bis(trifluoromethyl)benzyloxy)-4-amino-2-(2,4-dimethylphenyl)butan-2-ol, trifluoroacetic acid salt. Prepared as in General A, by using starting reagents (3,5-bis(trifluoromethyl)phenyl)methanol and 2,4-dimethylphenylmagnesium bromide. $^1$H NMR (500 MHz, MeOD) δ ppm 7.88 (s, 1 H) 7.87 (s, 2 H) 7.45 (d, J=7.93 Hz, 1 H) 6.97–7.05 (m, 2 H) 4.68–4.76 (m, 2 H) 3.85–3.91 (m, 2 H) 2.88–2.97 (m, 2 H) 2.47 (s, 3 H) 2.41 (ddd, J=14.19, 8.39, 5.80 Hz, 1 H) 2.30 (s, 3 H) 2.26–2.34 (m, 1 H); HRMS [ESI, MH$^+$] m/z calcd for $C_{21}H_{24}NO_2F_6$ 436.1711, found 436.1729.

EXAMPLE 31

1-(3,5-bis(trifluoromethyl)benzyloxy)-4-amino-2-(4-fluoro-2-methylphenyl)butan-2-ol, trifluoroacetic acid salt. Prepared as in General A, by using starting reagents (3,5-bis(trifluoromethyl)phenyl)methanol and 4-fluoro-2-methylphenylmagnesium bromide. $^1$H NMR (500 MHz, MeOD) δ ppm 7.88 (s, 3 H) 7.56–7.62 (m, 1 H) 6.90–6.96 (m, 2 H) 4.69–4.78 (m, 2 H) 3.86–3.91 (m, 2 H) 2.89–2.98 (m, 2 H) 2.51 (s, 3 H) 2.40 (ddd, J=14.27, 8.47, 5.95 Hz, 1 H) 2.26–2.34 (m, 1 H); HRMS [ESI, MH$^+$] m/z calcd for $C_{20}H_{21}NO_2F_7$ 440.1461, found 440.1473.

EXAMPLE 32

1-(3,5-bis(trifluoromethyl)benzyloxy)-4-amino-2-(3,4-dimethylphenyl)butan-2-ol, trifluoroacetic acid salt. Prepared as in General A, by using starting reagents (3,5-bis(trifluoromethyl)phenyl)methanol and 3,4-dimethylphenylmagnesium chloride. $^1$H NMR (500 MHz, MeOD) δ ppm 7.87 (s, 1 H) 7.86 (s, 2 H) 7.29 (s, 1 H) 7.19–7.26 (m, 1 H) 7.12–7.19 (m, 1 H) 4.65–4.74 (m, 2 H) 3.67–3.79 (m, 2 H) 2.92 (dt, J=12.74, 7.52 Hz, 1 H) 2.80 (ddd, J=12.67, 7.63, 5.34 Hz, 1 H) 2.30 (s, 3 H) 2.28 (s, 3 H) 2.26–2.35 (m, 1 H) 2.20 (ddd, J=13.89, 8.24, 5.34 Hz, 1 H); $^{13}$C NMR (126 MHz, MeOD) δ ppm 142.26 (s) 140.56 (s) 136.62 (s) 135.77 (s) 131.58 (q, $J_{CCF}$=33.96 Hz) 129.63 (s) 127.70 (s) 126.71 (s) 123.80 (q, $J_{CF}$=271.66 Hz) 123.03 (s) 121.16 (s) 78.75 (s) 75.98 (s) 71.73 (s) 36.08 (s) 35.50 (s) 19.03 (s) 18.34 (s); HRMS [ESI, MH$^+$] m/z calcd for $C_{21}H_{24}NO_2F_6$ 436.1711, found 436.1696.

EXAMPLE 33

1-(3,5-bis(trifluoromethyl)benzyloxy)-4-amino-2-(3-fluoro-4-methylphenyl)butan-2-ol, trifluoroacetic acid salt. Prepared as in General A, by using starting reagents (3,5-bis(trifluoromethyl)phenyl)methanol and 3-fluoro-4-methylphenylmagnesium bromide. $^1$H NMR (500 MHz, MeOD) δ ppm 7.88 (s, 1 H) 7.85 (s, 2 H) 7.22–7.28 (m, 2 H) 7.20 (dd, J=7.93, 1.83 Hz, 1 H) 4.67–4.75 (m, 2 H) 3.69–3.78 (m, 2 H) 2.93 (ddd, J=13.05, 7.78, 7.55 Hz, 1 H) 2.77–2.85 (m, 1 H) 2.31 (ddd, J=14.19, 7.93, 7.78 Hz, 1 H) 2.28 (s, 3 H) 2.19 (ddd, J=13.96, 8.32, 5.49 Hz, 1 H); $^{13}$C NMR (126 MHz, MeOD) δ ppm 159.13 (d, $J_{CF}$=879.13 Hz) 143.75 (s) 142.13 (s) 131.66 (q, $J_{CCF}$=40.25 Hz) 131.54 (s) 127.70 (s) 123.82 (q, $J_{CF}$=271.66 Hz) 121.23 (s) 121.11, 121.09, 112.36 (d, $J_{CCF}$=23.90 Hz) 78.33 (s) 75.67 (s) 71.71 (s) 35.93 (s) 35.54 (s) 13.08 (s); HRMS [ESI, MH$^+$] m/z calcd for $C_{20}H_{21}NO_2F_7$ 440.1461, found 440.1477.

EXAMPLE 34

1-(3,5-bis(trifluoromethyl)benzyloxy)-4-amino-2-(naphthalen-1-yl)butan-2-ol, trifluoroacetic acid salt. Prepared as in General A, by using starting reagents (3,5-bis(trifluoromethyl)phenyl)methanol and 1-naphthylmagnesium bromide. $^1$H NMR (500 MHz, MeOD) δ ppm 8.55 (d, J=5.19 Hz, 1 H) 7.93 (dd, J=6.71, 2.75 Hz, 1 H) 7.84 (s, 1 H) 7.83–7.89 (m, 2 H) 7.82 (s, 2 H) 7.47–7.53 (m, 3 H) 4.66–4.74 (m, 2 H) 3.93–4.37 (m, 2 H) 2.89–2.98 (m, 2 H) 2.75 (ddd, J=14.11, 8.01, 6.26 Hz, 1 H) 2.54 (ddd, J=14.50, 7.48, 7.32 Hz, 1 H); HRMS [ESI, MH$^+$] m/z calcd for $C_{23}H_{22}NO_2F_6$ 458.1555, found 458.1569.

EXAMPLE 35

1-(3,5-bis(trifluoromethyl)benzyloxy)-4-amino-2-(4-propylphenyl)butan-2-ol, trifluoroacetic acid salt. Prepared as in General A, by using starting reagents (3,5-bis(trifluoromethyl)phenyl)methanol and 4-propylphenylmagnesium bromide. $^1$H NMR (500 MHz, MeOD) δ ppm 7.88 (s, 3 H) 7.41–7.46 (m, 2 H) 7.23 (d, J=8.24 Hz, 2 H) 4.67–4.74 (m, 2 H) 3.69–3.81 (m, 2 H) 2.93 (ddd, J=12.67, 7.78, 7.63 Hz, 1 H) 2.81 (ddd, J=12.74, 7.71, 5.49 Hz, 1 H) 2.58–2.64 (m, 2 H) 2.34 (dt, J=14.11, 7.74 Hz, 1 H) 2.21 (ddd, J=13.89, 8.24, 5.34 Hz, 1 H) 1.62–1.70 (m, J=7.48, 7.48, 7.48, 7.32 Hz, 2 H) 0.96 (t, J=7.32 Hz, 3 H); $^{13}$C NMR (126 MHz, MeOD) δ ppm 142.23 (s) 142.10 (s) 140.52 (s) 131.64 (q, $J_{CCF}$=33.96 Hz) 128.54 (s) 127.73 (s) 125.53 (s) 123.80 (q, $J_{CF}$=271.66 Hz) 121.19 (s) 78.66 (s) 76.01 (s) 71.76 (s) 37.57 (s) 36.05 (s) 35.57 (s) 24.67 (s) 13.06 (s); HRMS [ESI, MH$^+$] m/z calcd for $C_{22}H_{26}NO_2F_6$ 450.1868, found 450.1887.

EXAMPLE 36

1-(3,5-bis(trifluoromethyl)benzyloxy)-4-amino-2-(3-fluoro-2-methylphenyl)butan-2-ol, trifluoroacetic acid salt. Prepared as in General A, by using starting reagents (3,5-bis(trifluoromethyl)phenyl)methanol and 3-fluoro-2-methylphenylmagnesium chloride. $^1$H NMR (500 MHz, MeOD) δ ppm 7.88 (s, 3 H) 7.42 (d, J=7.93 Hz, 1 H) 7.20–7.25 (m, 1 H) 7.04 (t, J=9.00 Hz, 1 H) 4.70–4.78 (m, 2 H) 3.90–3.94 (m, 2 H) 2.90–2.99 (m, 2 H) 2.41 (s, 3 H) 2.38–2.44 (m, 1 H) 2.28–2.35 (m, 1 H); HRMS [ESI, MH$^+$] m/z calcd for $C_{20}H_{21}NO_2F_7$ 440.1461, found 440.1454.

EXAMPLE 37

1-(3,5-bis(trifluoromethyl)benzyloxy)-4-amino-2-(2,5-dimethylphenyl)butan-2-ol, trifluoroacetic acid salt. Prepared as in General A, by using starting reagents (3,5-bis(trifluoromethyl)phenyl)methanol and 2,5-dimethylphenylmagnesium bromide. $^1$H NMR (500 MHz, MeOD) δ ppm 7.89 (s, 3 H) 7.46 (d, J=7.63 Hz, 1 H) 7.09–7.16 (m, 2 H) 4.70–4.77 (m, 2 H) 3.90–3.98 (m, 2 H) 2.94 (t, J=7.32 Hz, 2 H) 2.43–2.50 (m, 1 H) 2.41 (s, 3 H) 2.32–2.38 (m, 1 H) 2.29 (s, 3 H); $^{13}$C NMR (126 MHz, MeOD) δ ppm 142.18 (s) 140.32 (s) 138.82 (s) 134.30 (s) 131.64 (q, $J_{CCF}$=32.70 Hz) 129.64 (s) 127.83 (s) 125.35 (s) 125.18 (s) 123.81 (q, $J_{CF}$=271.66 Hz) 121.25 (s) 76.99 (s) 71.65 (s) 36.35 (s) 34.82 (s) 20.25 (s) 16.93 (s); HRMS [ESI, MH$^+$] m/z calcd for $C_{21}H_{24}NO_2F_6$ 436.1711, found 436.1721.

EXAMPLE 38

1-(3,5-bis(trifluoromethyl)benzyloxy)-4-amino-2-(4-ethylphenyl)butan-2-ol, trifluoroacetic acid salt. Prepared as in General A, by using starting reagents (3,5-bis(trifluoromethyl)phenyl)methanol and 4-ethylphenylmagnesium bromide. $^1$H NMR (500 MHz, MeOD) δ ppm 7.88 (s, 3 H) 7.38–7.46 (m, 2 H) 7.25 (d, J=8.24 Hz, 2 H) 4.66–4.74 (m, 2 H) 3.67–3.81 (m, 2 H) 2.93 (dt, J=12.89, 7.44 Hz, 1 H) 2.76–2.84 (m, 1 H) 2.61–2.70 (m, J=7.93, 7.71, 7.59, 7.59 Hz, 2 H) 2.33 (dt, J=14.11, 7.74 Hz, 1 H) 2.21 (ddd, J=13.96, 8.32, 5.49 Hz, 1 H) 1.25 (t, J=7.63 Hz, 3 H); $^{13}$C NMR (126 MHz, MeOD) δ ppm 143.77 (s) 142.23 (s) 140.48 (s) 131.63 (q, $J_{CCF}$=33.96 Hz) 127.91 (s) 127.74 (s) 125.61 (s) 123.86 (q, $J_{CF}$=271.66 Hz) 121.20 (s) 78.66 (s) 76.02 (s) 71.74 (s) 36.05 (s) 35.57 (s) 28.39 (s) 15.07 (s); HRMS [ESI, MH$^+$] m/z calcd for $C_{21}H_{24}NO_2F_6$ 436.1711, found 436.1716.

EXAMPLE 39

1-(3,5-bis(trifluoromethyl)benzyloxy)-4-amino-2-(3,4-dimethoxyphenyl)butan-2-ol, trifluoroacetic acid salt. Prepared as in General A, by using starting reagents (3,5-bis(trifluoromethyl)phenyl)methanol and 3,4-dimethoxyphenylmagnesium bromide. $^1$H NMR (500 MHz, MeOD) δ ppm 7.89 (s, 3 H) 7.16 (d, J=2.14 Hz, 1 H) 7.02–7.08 (m, 1 H) 6.94–7.02 (m, 1 H) 4.65–4.78 (m, 2 H) 3.86 (s, 3 H) 3.85 (s, 3 H) 3.66–3.83 (m, 2 H) 2.89–2.98 (m, 1 H) 2.74–2.87 (m, 1 H) 2.28–2.38 (m, 1 H) 2.21 (ddd, J=13.81, 8.01, 5.34 Hz, 1 H); HRMS [ESI, MH$^+$] m/z calcd for $C_{21}H_{24}NO_4F_6$ 468.1610, found 468.1621.

EXAMPLE 40

1-(3,5-bis(trifluoromethyl)benzyloxy)-4-amino-2-(4-chloro-2-methylphenyl)butan-2-ol, trifluoroacetic acid salt. Prepared as in General A, by using starting reagents (3,5-bis(trifluoromethyl)phenyl)methanol and 4-chloro-2-methylphenylmagnesium bromide. $^1$H NMR (500 MHz, MeOD) δ ppm 7.89 (s, 1 H) 7.87 (s, 2 H) 7.57 (d, J=9.16 Hz, 1 H) 7.07–7.29 (m, 2 H) 4.69–4.78 (m, 2 H) 3.86–3.92 (m, 2 H) 2.83–3.01 (m, 2 H) 2.50 (s, 3 H) 2.34–2.45 (m, 1 H) 2.22–2.33 (m, 1 H); HRMS [ESI, MH$^+$] m/z calcd for $C_{20}H_{21}NO_2F_6Cl$ 456.1165, found 456.1144.

EXAMPLE 41

1-(3,5-bis(trifluoromethyl)benzyloxy)-4-amino-2-(4-fluorophenyl)butan-2-ol, trifluoroacetic acid salt. Prepared as in General A, by using starting reagents (3,5-bis(trifluoromethyl)phenyl)methanol and 4-fluorophenylmagnesium bromide. $^1$H NMR (500 MHz, MeOD) δ ppm 7.89 (s, 1 H) 7.87 (s, 2 H) 7.53–7.58 (m, 2 H) 7.13 (t, J=8.70 Hz, 2 H) 4.69–4.75 (m, 2 H) 3.75–3.79 (m, 1 H) 3.71–3.74 (m, 1 H) 2.93 (ddd, J=12.97, 7.32, 7.17 Hz, 1 H) 2.78–2.84 (m, 1 H) 2.33 (dt, J=14.27, 7.67 Hz, 1 H) 2.21 (ddd, J=13.96, 8.32, 5.49 Hz, 1H); HRMS [ESI, MH$^+$] m/z calcd for $C_{19}H_{19}NO_2F_7$ 426.1304, found 426.1293.

EXAMPLE 42

1-(3,5-bis(trifluoromethyl)benzyloxy)-4-amino-2-(4-chlorophenyl)butan-2-ol, trifluoroacetic acid salt. Prepared as in General A, by using starting reagents (3,5-bis(trifluoromethyl)phenyl)methanol and 4-chlorophenylmagnesium bromide. $^1$H NMR (500 MHz, MeOD) δ ppm 7.88 (s, 1 H) 7.86 (s, 2 H) 7.53 (d, J=7.32 Hz, 2 H) 7.40 (d, J=7.93 Hz, 2 H) 4.68–4.75 (m, 2 H) 3.75 (q, J=9.46 Hz, 2 H) 2.89–2.98 (m, 1 H) 2.77–2.85 (m, 1 H) 2.33 (ddd, J=14.27, 7.48, 7.25 Hz, 1 H) 2.21 (ddd, J=13.66, 8.16, 5.34 Hz, 1 H); $^{13}$C NMR (126 MHz, MeOD) δ ppm 142.33 (s) 142.11 (s) 133.38 (s) 131.70 (q, $J_{CCF}$=32.70 Hz) 128.44 (s) 127.75 (s) 127.46 (s) 123.78 (q, $J_{CF}$=271.92 Hz) 121.24 (s) 78.27 (s) 75.71 (s) 71.73 (s) 35.89 (s) 35.57 (s); HRMS [ESI, MH$^+$] m/z calcd for $C_{19}H_{19}NO_2F_6Cl$ 442.1009, found 442.1004.

EXAMPLE 43

1-(3,5-bis(trifluoromethyl)benzyloxy)-4-amino-2-o-tolylbutan-2-ol, trifluoroacetic acid salt. Prepared as in General A, by using starting reagents (3,5-bis(trifluoromethyl)phenyl)methanol and o-tolylmagnesium bromide. $^1$H NMR (500 MHz, MeOD) δ ppm 7.89 (s, 3 H) 7.54–7.65 (m, 1 H) 7.17–7.24 (m, 3 H) 4.65–4.79 (m, 2 H) 3.91 (s, 2 H) 2.80–3.04 (m, 2 H) 2.52 (s, 3 H) 2.43 (ddd, J=14.11, 8.32, 5.65 Hz, 1 H) 2.26–2.36 (m, 1 H); HRMS [ESI, MH$^+$] m/z calcd for $C_{20}H_{22}NO_2F_6$ 422.1555, found 422.1557.

EXAMPLE 44

1-(3,5-bis(trifluoromethyl)benzyloxy)-4-amino-2-(thiophen-2-yl)butan-2-ol, trifluoroacetic acid salt. Prepared as in General A, by using starting reagents (3,5-bis(trifluoromethyl)phenyl)methanol and 2-thienyllithium. $^1$H NMR (500 MHz, MeOD) δ ppm 7.95 (s, 2 H) 7.90 (s, 1 H) 7.38 (dd, J=4.88, 1.22 Hz, 1 H) 7.07–7.11 (m, 1 H) 7.05 (dd, J=5.04, 3.51 Hz, 1 H) 4.76 (s, 2 H) 3.74–3.81 (m, 2 H) 3.00–3.09 (m, 1 H) 2.85–2.98 (m, 1 H) 2.32–2.47 (m, 1 H) 2.22 (ddd, J=113.96, 8.32, 5.49 Hz, 1 H); HRMS [ESI, MH$^+$] m/z calcd for $C_{17}H_{18}NO_2F_6S$ 414.0962, found 414.0965.

EXAMPLE 45

1-(3,5-bis(trifluoromethyl)benzyloxy)-4-amino-2-(2-methoxyphenyl)butan-2-ol, trifluoroacetic acid salt. Prepared as in General A, by using starting reagents (3,5-bis(trifluoromethyl)phenyl)methanol and 2-methoxyphenylmagnesium bromide. $^1$H NMR (500 MHz, MeOD) δ ppm 7.87 (s, 1 H) 7.82 (s, 2 H) 7.68 (dd, J=7.63, 1.53 Hz, 1 H) 7.28–7.38 (m, 1 H) 7.03 (ddd, J=14.65, 7.17, 1.07 Hz, 2 H) 4.54–4.76 (m, 2 H) 3.90–4.02 (m, 2 H) 3.80 (s, 3 H) 2.81–2.91 (m, 1 H) 2.70–2.82 (m, 1 H) 2.52–2.64 (m, 1 H) 2.21 (dt, J=14.11, 7.74 Hz, 1 H); HRMS [ESI, MH$^+$] m/z calcd for $C_{20}H_{22}NO_3F_6$ 438.1504, found 438.1521.

EXAMPLE 46

1-(3,5-bis(trifluoromethyl)benzyloxy)-4-amino-2-(2,4-dimethoxyphenyl)butan-2-ol, trifluoroacetic acid salt. Prepared as in General A, by using starting reagents (3,5-bis(trifluoromethyl)phenyl)methanol and 2,4-dimethoxyphenylmagnesium bromide. $^1$H NMR (500 MHz, MeOD) δ ppm 7.87 (s, 1 H) 7.83 (s, 2 H) 7.56 (d, J=8.55 Hz, 1 H) 6.58–6.62 (m, 1 H) 6.57 (d, J=2.14 Hz, 1 H) 4.66–4.74 (m, 1 H) 4.55–4.66 (m, 1 H) 3.90–3.97 (m, 1 H) 3.84–3.90 (m, 1 H) 3.82 (s, 3 H) 3.77 (s, 3 H) 2.80–2.92 (m, 1 H) 2.68–2.81 (m, 1 H) 2.47–2.58 (m, 1 H) 2.08–2.24 (m, 1 H); HRMS [ESI, MH$^+$] m/z calcd for $C_{21}H_{24}NO_4F_6$ 468.1610, found 468.1630.

EXAMPLE 47

4-amino-1-(benzyloxy)-2-phenylbutan-2-ol, trifluoroacetic acid salt. Prepared as in General A, by using starting reagents benzyl alcohol and phenylmagnesium chloride. $^1$H NMR (500 MHz, MeOD) δ ppm 7.52 (d, J=8.24 Hz, 2 H) 7.39 (t, J=7.78 Hz, 2 H) 7.27–7.35 (m, 6 H) 4.53–4.59 (m, 2 H) 3.66 (dd, J=46.54, 9.61 Hz, 2 H) 2.91 (ddd, J=13.05, 7.48, 7.25 Hz, 1 H) 2.78–2.85 (m, 1 H) 2.36 (ddd, J=14.42, 7.78, 7.40 Hz, 1 H) 2.17 (ddd, J=14.04, 8.09, 5.65 Hz, 1 H); HRMS [ESI, MH$^+$] m/z calcd for $C_{17}H_{22}NO_2$ 272.1651, found 272.1642.

EXAMPLE 48

1-(3-bromobenzyloxy)-4-amino-2-phenylbutan-2-ol, trifluoroacetic acid salt. Prepared as in General A, by using starting reagents 3-bromobenzyl alcohol and phenylmagnesium chloride. $^1$H NMR (500 MHz, MeOD) δ ppm 7.50–7.54 (m, 2 H) 7.47–7.49 (m, 1 H) 7.38–7.46 (m, 3 H) 7.32 (tt, J=7.32, 1.22 Hz, 1 H) 7.22–7.28 (m, 2 H) 4.54 (s, 2 H) 3.56–3.76 (m, 2 H) 2.92 (dt, J=12.82, 7.32 Hz, 1 H) 2.76–2.84 (m, 1 H) 2.30–2.39 (m, 1 H) 2.19 (ddd, J=14.04, 8.24, 5.49 Hz, 1 H); HRMS [ESI, MH$^+$] m/z calcd for $C_{17}H_{21}NO_2Br$ 350.0756, found 350.0771.

EXAMPLE 49

1-(4-(trifluoromethoxy)benzyloxy)-4-amino-2-phenylbutan-2-ol, trifluoroacetic acid salt. Prepared as in General A, by using starting reagents 4-(trifluoromethoxy)benzyl alcohol and phenylmagnesium chloride. $^1$H NMR (500 MHz, MeOD) δ ppm 7.48–7.54 (m, 2 H) 7.36–7.42 (m, 4 H) 7.31

(t, J=7.17 Hz, 1 H) 7.24 (d, J=7.63 Hz, 2 H) 4.58 (s, 2 H) 3.55–3.78 (m, 2 H) 2.88–2.96 (m, 1 H) 2.77–2.85 (m, 1 H) 2.31–2.40 (m, 1 H) 2.20 (ddd, J=13.89, 8.09, 5.49 Hz, 1 H); $^{13}$C NMR (126 MHz, MeOD) δ ppm 148.91 (s) 143.57 (s) 137.81 (s) 129.39 (s) 128.41 (s) 127.41 (s) 125.58 (s) 120.94 (q, $J_{CF}$=255.31 Hz) 120.93 (s) 78.09 (s) 75.96 (s) 72.54 (s) 36.10 (s) 35.70 (s); HRMS [ESI, MH$^+$] m/z calcd for $C_{18}H_{21}NO_3F_3$ 356.1474, found 356.1479.

EXAMPLE 50

1-(2-chlorobenzyloxy)-4-amino-2-phenylbutan-2-ol, trifluoroacetic acid salt. Prepared as in General A, by using starting reagents 2-chlorobenzyl alcohol and phenylmagnesium chloride. $^1$H NMR (500 MHz, MeOD) δ ppm 7.54 (d, J=7.63 Hz, 2 H) 7.42–7.47 (m, 1 H) 7.40 (t, J=7.63 Hz, 3 H) 7.27–7.33 (m, 3 H) 4.64–4.69 (m, 2 H) 3.64–3.84 (m, 2 H) 2.90–2.97 (m, 1 H) 2.80–2.87 (m, 1 H) 2.36–2.43 (m, 1 H) 2.21 (ddd, J=14.11, 8.16, 5.49 Hz, 1 H); $^{13}$C NMR (126 MHz, MeOD) δ ppm 143.58 (s) 135.96 (s) 133.17 (s) 129.73 (s) 129.34 (s) 129.20 (s) 128.42 (s) 127.42 (s) 127.02 (s) 125.58 (s) 78.37 (s) 75.95 (s) 70.66 (s) 36.12 (s) 35.75 (s); HRMS [ESI, MH$^+$] m/z calcd for $C_{17}H_{21}NO_2Cl$ 306.1261, found 306.1254.

EXAMPLE 51

1-(3-fluoro-5-(trifluoromethyl)benzyloxy)-4-amino-2-phenylbutan-2-ol, trifluoroacetic acid salt. Prepared as in General A, by using starting reagents 3-fluoro-5-(trifluoromethyl)benzyl alcohol and phenylmagnesium chloride. $^1$H NMR (500 MHz, MeOD) δ ppm 7.49–7.56 (m, 2 H) 7.41 (s, 1 H) 7.41 (dd, J=14.80, 7.17 Hz, 2 H) 7.29–7.36 (m, 3 H) 4.59–4.67 (m, 2 H) 3.74–3.78 (m, 1 H) 3.70 (d, J=9.46 Hz, 1 H) 2.94 (ddd, J=112.97, 7.48, 7.32 Hz, 1 H) 2.77–2.85 (m, 1 H) 2.32–2.41 (m, 1 H) 2.23 (ddd, J=13.96, 8.32, 5.49 Hz, 1 H); $^{13}$C NMR (126 MHz, MeOD) δ ppm 163.01 (d, $J_{CF}$=247.77 Hz) 143.50 (d, J=7.55 Hz) 143.35 (s) 132.18 (dd, J=32.70, 7.55 Hz) 128.44 (s) 127.45 (s) 125.61 (s) 123.78 (dq, J=271.66, 3.77 Hz) 119.84 (s) 119.84 (d, J=7.55 Hz) 117.97 (d, J=22.64 Hz) 111.42 (dd, J=23.90, 3.77 Hz) 78.46 (s) 76.01 (s) 71.89 (s) 36.03 (s) 35.62 (s); HRMS [ESI, MH$^+$] m/z calcd for $C_{18}H_{20}NO_2F_4$ 358.1430, found 358.1447.

EXAMPLE 52

1-(2-bromobenzyloxy)-4-amino-2-phenylbutan-2-ol, trifluoroacetic acid salt. Prepared as in General A, by using starting reagents 2-bromobenzyl alcohol and phenylmagnesium chloride. $^1$H NMR (500 MHz, MeOD) δ ppm 7.52–7.58 (m, 3 H) 7.37–7.45 (m, 3 H) 7.29–7.35 (m, 2 H) 7.21 (t, J=7.48 Hz, 1 H) 4.64 (s, 2 H) 3.75 (dd, J=50.51, 9.61 Hz, 2 H) 2.90–2.97 (m, 1 H) 2.80–2.87 (m, 1 H) 2.40 (ddd, J=14.57, 7.63, 7.40 Hz, 1 H) 2.22 (ddd, J=13.89, 8.09, 5.49 Hz, 1 H); $^{13}$C NMR (126 MHz, MeOD) δ ppm 143.56 (s) 137.59 (s) 132.67 (s) 129.80 (s) 129.43 (s) 128.43 (s) 127.60 (s) 127.43 (s) 125.59 (s) 122.87 (s) 78.36 (s) 75.97 (s) 72.94 (s) 36.14 (s) 35.76 (s); HRMS [ESI, MH$^+$] m/z calcd for $C_{17}H_{21}NO_2Br$ 350.0756, found 350.0755.

EXAMPLE 53

1-(3,5-dimethylbenzyloxy)-4-amino-2-phenylbutan-2-ol, trifluoroacetic acid salt. Prepared as in General A, by using starting reagents 3,5-dimethylbenzyl alcohol and phenylmagnesium chloride. $^1$H NMR (500 MHz, MeOD) δ ppm 7.46–7.53 (m, 2 H) 7.36–7.41 (m, 2 H) 7.31 (tt, J=7.32, 1.22 Hz, 1 H) 6.93 (s, 1 H) 6.89 (s, 2 H) 4.48 (s, 2 H) 3.53–3.71 (m, 2 H) 2.91 (dt, J=12.89, 7.44 Hz, 1 H) 2.77–2.84 (m, 1 H) 2.34 (dt, J=14.19, 7.17 Hz, 1 H) 2.28 (s, 6 H) 2.17 (ddd, J=114.04, 8.09, 5.65 Hz, 1 H); HRMS [ESI, MH$^+$] m/z calcd for $C_{19}H_{26}NO_2$ 300.1964, found 300.1975.

EXAMPLE 54

1-(2-(trifluoromethyl)benzyloxy)-4-amino-2-phenylbutan-2-ol, trifluoroacetic acid salt. Prepared as in General A, by using starting reagents 2-(trifluoromethyl)benzyl alcohol and phenylmagnesium chloride. $^1$H NMR (500 MHz, MeOD) δ ppm 7.68 (d, J=7.63 Hz, 1 H) 7.62–7.64 (m, 1 H) 7.52–7.60 (m, 3 H) 7.46 (t, J=7.17 Hz, 1 H) 7.41 (t, J=7.63 Hz, 2 H) 7.32 (t, J=6.71 Hz, 1 H) 4.75 (s, 2 H) 3.62–3.83 (m, 2 H) 2.89–2.97 (m, 1 H) 2.78–2.86 (m, 1 H) 2.35–2.43 (m, 1 H) 2.23 (ddd, J=14.04, 8.09, 5.65 Hz, 1 H); $^{13}$C NMR (126 MHz, MeOD) δ ppm 143.45 (s) 137.02 (s) 132.32 (s) 129.61 (s) 128.44 (s) 127.89 (s) 127.70 (s) 127.44 (s) 125.72 (q, $J_{CCF}$=6.29 Hz) 125.61 (s) 124.88 (q, $J_{CF}$=272.92 Hz) 78.58 (s) 75.98 (s) 69.60 (s) 36.08 (s) 35.66 (s); HRMS [ESI, MH$^+$] m/z calcd for $C_{18}H_{21}NO_2F_3$ 340.1524, found 340.1541.

EXAMPLE 55

1-(3-(trifluoromethyl)benzyloxy)-4-amino-2-phenylbutan-2-ol, trifluoroacetic acid salt. Prepared as in General A, by using starting reagents 3-(trifluoromethyl)benzyl alcohol and phenylmagnesium chloride. $^1$H NMR (500 MHz, MeOD) δ ppm 7.60 (d, J=10.68 Hz, 2 H) 7.51–7.56 (m, 4 H) 7.40 (t, J=7.63 Hz, 2 H) 7.32 (t, J=7.17 Hz, 1 H) 4.64 (s, 2 H) 3.63–3.80 (m, 2 H) 2.87–2.96 (m, 1 H) 2.76–2.84 (m, 1 H) 2.36 (ddd, J=14.34, 7.63, 7.32 Hz, 1 H) 2.21 (ddd, J=14.11, 8.16, 5.49 Hz, 1 H); HRMS [ESI, MH$^+$] m/z calcd for $C_{18}H_{21}NO_2F_3$ 340.1524, found 340.1533.

EXAMPLE 56

1-(4-(trifluoromethyl)benzyloxy)-4-amino-2-phenylbutan-2-ol, trifluoroacetic acid salt. Prepared as in General A, by using starting reagents 4-(trifluoromethyl)benzyl alcohol and phenylmagnesium chloride. $^1$H NMR (500 MHz, MeOD) δ ppm 7.62 (d, J=7.93 Hz, 2 H) 7.54 (d, J=7.93 Hz, 2 H) 7.48 (d, J=7.63 Hz, 2 H) 7.40 (t, J=7.63 Hz, 2 H) 7.31 (t, J=7.32 Hz, 1 H) 4.64 (s, 2 H) 3.72–3.77 (m, 1 H) 3.64–3.69 (m, 1 H) 2.90–2.98 (m, 1 H) 2.79–2.86 (m, 1 H) 2.39 (ddd, J=14.50, 7.48, 7.32 Hz, 1 H) 2.22 (ddd, J=13.96, 8.32, 5.49 Hz, 1 H); $^{13}$C NMR (126 MHz, MeOD) δ ppm 143.51 (s) 143.15 (s) 129.79 (q, J=31.44 Hz) 128.43 (s) 127.98 (s) 127.41 (s) 125.61 (s) 125.09 (q, $J_{CCF}$=47.79 Hz) 124.72 (q, $J_{CF}$=270.41 Hz) 78.29 (s) 75.98 (s) 72.60 (s) 36.09 (s) 35.70 (s); HRMS [ESI, MH$^+$] m/z calcd for $C_{18}H_{21}NO_2F_3$ 340.1524, found 340.1539.

EXAMPLE 57

1-(2-fluorobenzyloxy)-4-amino-2-phenylbutan-2-ol, trifluoroacetic acid salt. Prepared as in General A, by using starting reagents 2-fluorobenzyl alcohol and phenylmagnesium chloride. $^1$H NMR (500 MHz, MeOD) δ ppm 7.52 (d, J=7.93 Hz, 2 H) 7.25–7.43 (m, 5 H) 7.16 (t, J=7.48 Hz, 1 H) 7.04–7.12 (m, 1 H) 4.59–4.66 (m, 2 H) 3.70 (dd, J=50.81, 9.61 Hz, 2 H) 2.92 (ddd, J=12.97, 7.48, 7.32 Hz, 1 H) 2.77–2.85 (m, 1 H) 2.36 (ddd, J=14.34, 7.63, 7.32 Hz, 1 H) 2.18 (ddd, J=13.96, 8.16, 5.65 Hz, 1 H); $^{13}$C NMR (126

MHz, MeOD) δ ppm 161.26 (d, $J_{CF}$=245.25 Hz) 143.60 (s) 130.58 (d, J=5.03 Hz) 129.90 (d, J=8.80 Hz) 128.41 (s) 127.41 (s) 125.52 (s) 125.26(d, J=15.09 Hz) 124.28 (d, J=3.77 Hz) 115.13 (d, J=22.64 Hz) 78.11 (s) 75.89 (s) 67.08 (d, J=3.77 Hz) 36.10 (s) 35.73 (s); HRMS [ESI, MH$^+$] m/z calcd for $C_{17}H_{21}NO_2F$ 290.1556, found 290.1555.

EXAMPLE 58

1-(3-fluorobenzyloxy)-4-amino-2-phenylbutan-2-ol, trifluoroacetic acid salt. Prepared as in General A, by using starting reagents 3-fluorobenzyl alcohol and phenylmagnesium chloride. $^1$H NMR (500 MHz, MeOD) δ ppm 7.53 (d, J=7.32 Hz, 2 H) 7.40 (t, J=7.48 Hz, 2 H) 7.29–7.36 (m, 2 H) 7.10 (d, J=7.32 Hz, 1 H) 6.98–7.07 (m, 2 H) 4.56 (s, 2 H) 3.58–3.77 (m, 2 H) 2.89–2.96 (m, 1 H) 2.78–2.85 (m, 1 H) 2.33–2.41 (m, 1 H) 2.20 (ddd, J=14.04, 8.24, 5.49 Hz, 1 H); $^{13}$C NMR (126 MHz, MeOD) δ ppm 163.35 (d, $J_{CF}$=243.99 Hz) 143.53 (s) 141.44 (d, J=7.55 Hz) 130.12 (d, J=8.80 Hz) 128.41 (s) 127.41 (s) 125.58 (s) 123.28 (d, J=2.52 Hz) 114.34 (d, J=8.80 Hz) 114.17 (d, J=10.06 Hz) 78.10 (s) 75.96 (s) 72.68 (s) 36.09 (s) 35.70 (s); HRMS [ESI, MH$^+$] m/z calcd for $C_{17}H_{21}NO_2F$ 290.1556, found 290.1564.

EXAMPLE 59

1-(4-fluorobenzyloxy)-4-amino-2-phenylbutan-2-ol, trifluoroacetic acid salt. Prepared as in General A, by using starting reagents 4-fluorobenzyl alcohol and phenylmagnesium chloride. $^1$H NMR (500 MHz, MeOD) δ ppm 7.51 (d, J=7.93 Hz, 2 H) 7.39 (t, J=7.63 Hz, 2 H) 7.27–7.36 (m, 3 H) 7.00–7.08 (m, 2 H) 4.53 (s, 2 H) 3.56–3.74 (m, 2 H) 2.86–2.95 (m, 1 H) 2.76–2.84 (m, 1 H) 2.35 (ddd, J=14.50, 7.48, 7.32 Hz, 1 H) 2.18 (ddd, J=13.89, 8.09, 5.49 Hz, 1 H); $^{13}$C NMR (126 MHz, MeOD) δ ppm 162.80 (d, $J_{CF}$=245.25 Hz) 143.62 (s) 134.47 (d, J=2.52 Hz) 129.85 (d, J=7.55 Hz) 128.40 (s) 127.39 (s) 125.56 (s) 115.02 (d, J=22.64 Hz) 77.85 (s) 75.94 (s) 72.76 (s) 36.11 (s) 35.73 (s); HRMS [ESI, MH$^+$] m/z calcd for $C_{17}H_{21}NO_2F$ 290.1556, found 290.1551.

EXAMPLE 60

1-(3-methylbenzyloxy)-4-amino-2-phenylbutan-2-ol, trifluoroacetic acid salt. Prepared as in General A, by using starting reagents 3-methylbenzyl alcohol and phenylmagnesium chloride. $^1$H NMR (500 MHz, MeOD) δ ppm 7.52 (d, J=7.93 Hz, 2 H) 7.35–7.41 (m, 2 H) 7.27–7.35 (m, 1 H) 7.16–7.23 (m, 1 H) 7.05–7.12 (m, 3 H) 4.47–4.54 (m, 2 H) 3.55–3.75 (m, 2 H) 2.91 (dt, J=12.89, 7.44 Hz, 1 H) 2.77–2.84 (m, 1 H) 2.33 (s, 3 H) 2.29–2.38 (m, 1 H) 2.17 (ddd, J=14.04, 8.09, 5.65 Hz, 1 H); HRMS [ESI, MH$^+$] m/z calcd for $C_{18}H_{24}NO_2$ 286.1807, found 286.1819.

EXAMPLE 61

1-(3,5-dichlorobenzyloxy)-4-amino-2-phenylbutan-2-ol, trifluoroacetic acid salt. Prepared as in General A, by using starting reagents 3,5-dichlorobenzyl alcohol and phenylmagnesium chloride. $^1$H NMR (500 MHz, MeOD) δ ppm 7.53 (d, J=8.24 Hz, 2 H) 7.41 (s, 1 H) 7.41 (t, J=7.78 Hz, 1 H) 7.29–7.37 (m, 2 H) 7.25 (s, 2 H) 4.49–4.57 (m, 2 H) 3.73 (d, J=9.50 Hz, 1 H) 3.66 (d, J=9.46 Hz, 1 H) 2.93 (ddd, J=12.82, 7.78, 7.48 Hz, 1 H) 2.76–2.84 (m, 1 H) 2.31–2.39 (m, 1 H) 2.21 (ddd, J=13.96, 8.32, 5.49 Hz, 1 H); $^{13}$C NMR (126 MHz, MeOD) δ ppm 143.36 (s) 142.74 (s) 135.08 (s) 128.46 (s) 127.48 (s) 127.44 (s) 125.96 (s) 125.60 (s) 78.30 (s) 76.00 (s) 71.86 (s) 36.05 (s) 35.62 (s); HRMS [ESI, MH$^+$] m/z calcd for $C_{17}H_{20}NO_2Cl_2$ 340.0871, found 340.0880.

EXAMPLE 62

1-(2-methoxybenzyloxy)-4-amino-2-phenylbutan-2-ol, trifluoroacetic acid salt. Prepared as in General A, by using starting reagents 2-methoxybenzyl alcohol and phenylmagnesium chloride. $^1$H NMR (500 MHz, MeOD) δ ppm 7.47–7.54 (m, 2 H) 7.35–7.41 (m, 2 H) 7.26–7.35 (m, 3 H) 6.95–7.02 (m, 1 H) 6.87–6.95 (m, 1 H) 4.55–4.63 (m, 2 H) 3.84 (s, 3 H) 3.70 (dd, J=57.53, 9.61 Hz, 2 H) 2.93 (ddd, J=13.12, 7.32, 7.02 Hz, 1 H) 2.84 (ddd, J=12.67, 6.56, 6.41 Hz, 1 H) 2.36 (ddd, J=14.50, 7.48, 7.32 Hz, 1 H) 2.16 (ddd, J=14.04, 7.78, 5.65 Hz, 1 H); HRMS [ESI, MH$^+$] m/z calcd for $C_{18}H_{24}NO_3$ 302.1756, found 302.1771.

EXAMPLE 63

1-(3-methoxybenzyloxy)-4-amino-2-phenylbutan-2-ol, trifluoroacetic acid salt. Prepared as in General A, by using starting reagents 3-methoxybenzyl alcohol and phenylmagnesium chloride. $^1$H NMR (500 MHz, MeOD) δ ppm 7.52 (d, J=8.24 Hz, 2 H) 7.36–7.42 (m, 2 H) 7.28–7.34 (m, 1 H) 7.20–7.27 (m, 1 H) 6.82–6.89 (m, 3 H) 4.53 (s, 2 H) 3.78 (s, 3 H) 3.58–3.73 (m, 2 H) 2.87–2.96 (m, 1 H) 2.72–2.86 (m, 1 H) 2.35 (ddd, J=14.50, 7.48, 7.32 Hz, 1 H) 2.18 (ddd, J=14.04, 8.09, 5.65 Hz, 1 H); HRMS [ESI, MH$^+$] m/z calcd for $C_{18}H_{24}NO_3$ 302.1756, found 302.1768.

EXAMPLE 64

1-(3,5-difluorobenzyloxy)-4-amino-2-phenylbutan-2-ol, trifluoroacetic acid salt. Prepared as in General A, by using starting reagents 3,5-difluorobenzyl alcohol and phenylmagnesium chloride. $^1$H NMR (500 MHz, MeOD) δ ppm 7.48–7.55 (m, 2 H) 7.37–7.43 (m, 2 H) 7.32 (t, J=7.32 Hz, 1 H) 6.82–6.91 (m, 3 H) 4.56 (s, 2 H) 3.70 (dd, J=43.03, 9.46 Hz, 2 H) 2.93 (dt, J=12.82, 7.48 Hz, 1 H) 2.81 (ddd, J=12.82, 7.78, 5.65 Hz, 1 H) 2.32–2.40 (m, 1 H) 2.21 (ddd, J=13.96, 8.32, 5.49 Hz, 1 H); HRMS [ESI, MH$^+$] m/z calcd for $C_{17}H_{20}NO_2F_2$ 308.1462, found 308.1476.

EXAMPLE 65

1-(3-chlorobenzyloxy)-4-amino-2-phenylbutan-2-ol, trifluoroacetic acid salt. Prepared as in General A, by using starting reagents 3-chlorobenzyl alcohol and phenylmagnesium-chloride. $^1$H NMR-(500 MHz, MeOD) δ ppm 7.47–7.54 (m, 2 H) 7.36–7.42 (m, 2 H) 7.25–7.33 (m, 4 H) 7.18–7.23 (m, 1 H) 4.55 (s, 2 H) 3.58–3.77 (m, 2 H) 2.92 (dt, J=12.82, 7.48 Hz, 1 H) 2.76–2.84 (m, 1 H) 2.30–2.39 (m, 1 H) 2.19 (ddd, J=13.89, 8.09, 5.49 Hz, 1 H); HRMS [ESI, MH$^+$] m/z calcd for $C_{17}H_{21}NO_2Cl$ 306.1261, found 306.1276.

EXAMPLE 66

1-(4-bromobenzyloxy)-4-amino-2-phenylbutan-2-ol, trifluoroacetic acid salt. Prepared as in General A, by using starting reagents 4-bromobenzyl alcohol and phenylmagnesium chloride. $^1$H NMR (500 MHz, MeOD) δ ppm 7.45–7.53 (m, 4 H) 7.36–7.44 (m, 2 H) 7.31 (tt, J=7.32, 1.22 Hz, 1 H) 7.17–7.25 (m, 2 H) 4.52 (s, 2 H) 3.57–3.75 (m, 2 H) 2.92 (dt, J=12.82, 7.48 Hz, 1 H) 2.76–2.84 (m, 1 H)

2.30–2.38 (m, 1 H) 2.18 (ddd, J=13.96, 8.16, 5.65 Hz, 1 H); HRMS [ESI, MH$^+$] m/z calcd for $C_{17}H_{21}NO_2Br$ 350.0756, found 350.0827.

EXAMPLE 67

1-(2-methylbenzyloxy)-4-amino-2-phenylbutan-2-ol, trifluoroacetic acid salt. Prepared as in General A, by using starting reagents 2-methylbenzyl alcohol and phenylmagnesium chloride. $^1$H NMR (500 MHz, MeOD) δ ppm 7.45–7.52 (m, 2 H) 7.35–7.40 (m, 2 H) 7.24–7.32 (m, 2 H) 7.11–7.21 (m, 3 H) 4.56 (s, 2 H) 3.59–3.76 (m, 2 H) 2.90 (dt, J=12.82, 7.17 Hz, 1 H) 2.73–2.84 (m, 1 H) 2.29–2.38 (m, 1 H) 2.25 (s, 3 H) 2.17 (ddd, J=13.96, 8.01, 5.80 Hz, 1 H); HRMS [ESI, MH$^+$] m/z calcd for $C_{18}H_{24}NO_2$ 286.1807, found 286.1800.

EXAMPLE 68

1-(3,5-dibromobenzyloxy)-4-amino-2-phenylbutan-2-ol, trifluoroacetic acid salt. Prepared as in General A, by using starting reagents 3,5-dibromobenzyl alcohol and phenylmagnesium chloride. $^1$H NMR (500 MHz, MeOD) δ ppm 7.63 (s, 1 H) 7.53 (d, J=7.32 Hz, 2 H) 7.44 (s, 2 H) 7.38–7.45 (m, 2 H) 7.32 (t, J=6.87 Hz, 1 H) 4.49–4.56 (m, 2 H) 3.60–3.76 (m, 2 H) 2.88–2.96 (m, 1 H) 2.76–2.84 (m, 1 H) 2.31–2.38 (m, 1 H) 2.21 (ddd, J=13.89, 8.09, 5.49 Hz, 1 H); $^{13}$C NMR (126 MHz, MeOD) δ ppm 143.35 (s) 143.19 (s) 133.02 (s) 129.36 (s) 128.47 (s) 127.49 (s) 125.59 (s) 122.86 (s) 78.30 (s) 76.00 (s) 71.76 (s) 36.04 (s) 35.62 (s); HRMS [ESI, MH$^+$] m/z calcd for $C_{17}H_{20}NO_2Br_2$ 427.9861, found 427.9874.

EXAMPLE 69

1-(3-(trifluoromethoxy)benzyloxy)-4-amino-2-phenylbutan-2-ol, trifluoroacetic acid salt. Prepared as in General A, by using starting reagents 3-(trifluoromethoxy)benzyl alcohol and phenylmagnesium chloride. $^1$H NMR (500 MHz, MeOD) δ ppm 7.53 (d, J=7.94 Hz, 2 H) 7.41 (ddd, J=13.05, 7.93, 7.71 Hz, 3 H) 7.24–7.33 (m, 2 H) 7.16–7.23 (m, 2 H) 4.60 (s, 2 H) 3.61–3.78 (m, 2 H) 2.88–2.96 (m, 1 H) 2.76–2.85 (m, 1 H) 2.36 (ddd, J=14.57, 7.63, 7.40 Hz, 1 H) 2.21 (ddd, J=13.89, 8.09, 5.49 Hz, 1 H); $^{13}$C NMR (126 MHz, MeOD) δ ppm 149.66 (s) 143.50 (s) 141.38 (s) 130.05 (s) 128.42 (s) 127.42 (s) 126.22 (s) 125.59 (s) 120.92 (q, $J_{CF}$=255.31 Hz) 120.04 (s) 120.02 (s) 78.21 (s) 75.98 (s) 72.51 (s) 36.08 (s) 35.67 (s); HRMS [ESI, MH$^+$] m/z calcd for $C_{18}H_{21}NO_3F_3$ 356.1474, found 356.1477.

EXAMPLE 70

1-(4-chlorobenzyloxy)-4-amino-2-phenylbutan-2-ol, trifluoroacetic acid salt. Prepared as in General A, by using starting reagents 4-chlorobenzyl alcohol and phenylmagnesium chloride. $^1$H NMR (500 MHz, MeOD) δ ppm 7.52 (d, J=7.93 Hz, 2 H) 7.36–7.41 (m, 2 H) 7.26–7.34 (m, 5 H) 4.54 (s, 2 H) 3.53–3.76 (m, 2 H) 2.87–2.95 (m, 1 H) 2.76–2.84 (m, 1 H) 2.30–2.39 (m, J=7.78, 7.40, 7.21, 7.21 Hz, 1 H) 2.18 (ddd, J=13.89, 8.09, 5.49 Hz, 1 H); $^{13}$C NMR (126 MHz, MeOD) δ ppm 143.58 (s) 137.30 (s) 133.46 (s) 129.38 (s) 128.46 (s) 128.41 (s) 127.40 (s) 125.58 (s) 77.98 (s) 75.95 (s) 72.66 (s) 36.10 (s) 35.72 (s); HRMS [ESI, MH$^+$] m/z calcd for $C_{17}H_{21}NO_2Cl$ 306.1261, found 306.1267.

EXAMPLE 71

1-(3,5-bis(trifluoromethyl)benzyloxy)-4-amino-2-phenylbutane, trifluoroacetic acid salt. 4-(3,5-bis(trifluoromethyl)benzyloxy)-3-phenylbutanenitrile (41 mg, 0.106 mmol) was dissolved in a mixture of anhydrous THF and methylene chloride (200 ul:500 ul) and neat borane dimethylsulfide (1 ml) was added. The mixture was heated at 80° C. for 3 hours until completion of the reaction. It was cooled to room temperature and excess reagent was removed under nitrogen stream. Methanol was added to the residue and the mixture was heated at 80° C. for another 30 minutes. After concentration, 40% of the residue was submitted for preparative HPLC to give 11.4 mg of the desired product as a trifluoroacetic acid salt. $^1$H NMR (500 MHz, MeOD) δ ppm 2.06 (m, 1 H) 2.25 (m, 1 H) 2.76 (m, 1 H) 2.91 (m, 1 H) 3.09 (m, 1 H) 3.77 (m, 2 H) 4.69 (s, 2 H) 7.34 (m, 5 H) 7.86 (s, 2 H) 7.89 (s, 1 H); $^{13}$C NMR (500 MHz, MeOD) δ 142.41, 141.14, 131.70 (q, $J_{CCF}$=33.6 Hz), 128.88, 127.92, 127.59, 127.35, 123.84 (q, $J_{CF}$=271.6 Hz), 121.16, 75.26, 71.28, 43.87, 38.28, 30.47; HRMS [ESI, MH$^+$] m/z calcd for $C_{19}H_{20}F_6NO$ 392.1449, found 392.1457.

EXAMPLE 72

1-(3,5-bis(trifluoromethyl)benzyloxy)-4-methylamino-2-phenylbutane, trifluoroacetic acid salt. 1-(4-chlorobenzyloxy)-4-amino-2-phenylbutan-2-ol trifluoroacetic acid salt (42 mg, 0.083 mmol) was stirred with $K_2CO_3$ (114 mg, 0.83 mmol) and methyl chloroformate (23.6 mg, 0.249 mmol) in anhydrous methylene chloride (2 ml) at room temperature for 2 hours. It was quenched with water, extracted with methylene chloride. The organic phase was dried ($Na_2SO_4$) and concentrated to dryness. After re-dissolved in anhydrous THF (2 ml) and it was treated with lithium aluminum hydride (1 M, 0.244 ml, 0.244 mmol) at 90° C. for 2 hours. The reaction mixture was cooled to room temperature, acidified with aqueous hydrogen chloride solution and then basified with aqueous ammonia solution. It was then extracted with ethyl acetate, concentrated, and purified by preparative HPLC to give 7.5 mg of the desired product as a trifluoroacetic acid salt. $^1$H NMR (500 MHz, MeOD) δ ppm 2.08 (m, 1 H) 2.28 (m, 1 H) 2.65 (s, 3 H) 2.83 (m, 1 H) 3.01 (m, 1 H) 3.08 (m, 1 H) 3.76 (m, 2 H) 4.68 (s, 2 H) 7.34 (m, 5 H) 7.86 (s, 2 H) 7.89 (s, 1 H); $^{13}$C NMR (500 MHz, MeOD) δ 142.36, 140.98, 131.72 (q, $J_{CCF}$=33.6 Hz), 128.90, 127.89, 127.58, 127.38, 123.82 (q, $J_{CF}$=272.5 Hz), 121.15, 75.18, 71.31, 43.90, 32.50, 29.02; HRMS [ESI, MH$^+$] m/z calcd for $C_{20}H_{22}F_6NO$ 406.1606, found 406.1624.

EXAMPLE 73

1-(3,5-bis(trifluoromethyl)benzyloxy)-4-dimethylamino-2-phenylbutane, trifluoroacetic acid salt. 4-(3,5-bis(trifluoromethyl)benzyloxy)-3-phenylbutanenitrile (41 mg, 0.106 mmol) was dissolved in a mixture of anhydrous THF and methylene chloride (200 ul:500 ul) and neat borane dimethylsulfide (1 ml) was added. The mixture was heated at 80° C. for 3 hours until completion of the reaction. It was cooled to room temperature and excess reagent was removed under nitrogen stream. Methanol was added to the residue and the mixture was heated at 80° C. for another 30 minutes. After concentration, 60% of the residue was re-dissolved in methanol (1 ml). Excess formaldehyde (41 mg, 37 wt % aq., 0.5 mmol) was added and followed by addition of sodium borohydride (19 mg, 0.5 mmol). The reaction took place immediately with release of heat. After another 30 minutes of stirring, it was quenched with water, extracted with ethyl acetate and concentrated. The residue was purified by preparative HPLC to obtain 17 mg of the desired product as a trifluoroacetic acid salt. $^1$H NMR (500 MHz, MeOD) δ ppm 2.14 (m, 1 H) 2.32 (m, 1 H) 2.85 (s, 3 H) 2.87 (s, 3 H) 2.91 (m, 1 H) 3.08 (m, 1 H) 3.19 (m, 1 H) 3.77 (m, 2 H) 4.68 (m, 2 H) 7.34(m, 5 H) 7.89 (s, 1 H); $^{13}$C NMR (500 MHz, MeOD) δ 142.38, 140.86, 131.68 (q, $J_{CCF}$=33.6 Hz), 128.95, 127.92, 127.59, 127.45, 123.86 (q, $J_{CF}$=271.6 Hz), 75.17, 71.26, 56.68, 43.99, 42.52, 42.24, 27.48; HRMS [ESI, MH$^+$] m/z calcd for $C_{21}H_{24}F_6NO$ 420.1762, found 420.1770.

EXAMPLE 74

1-(3,5-bis(trifluoromethyl)benzyloxy)-4-amino-2-methyl-2-phenylbutane, trifluoroacetic acid salt. 4-(3,5-bis(trifluoromethyl)benzyloxy)-3-methyl-3-phenylbutanenitrile 4-(3,5-bis(trifluoromethyl)benzyloxy)-3-methyl-3-phenylbutanenitrile (12 mg, 0.030 mmol) was dissolved in small amount of THF (100 ul) and neat borane-dimethylsulfide complex (1 ml) was added. The mixture was heated at 80° C. for 1.5 hours until completion of the reduction. Afterwards excess borane was removed under nitrogen stream, the residue was quenched with methanol and heated at 80° C. for 1 hour. 40% of the crude mixture was purified by preparative HPLC to give 1.1 mg of the desired product as a trifluoroacetic acid salt. $^1$H NMR (500 MHz, MeOD) δ ppm 1.49 (s, 3 H) 2.09 (m, 1 H) 2.27 (m, 1 H) 2.66 (m, 2 H) 2.84 (m, 1 H) 3.65 (d, J=9.16 Hz, 1 H) 3.72 (d, J=8.85 Hz, 1 H) 4.68 (s, 2 H) 7.28 (t, J=7.17 Hz, 1 H) 7.38 (m, 2 H) 7.45 (m, 2 H) 7.84 (s, 2 H) 7.89 (s, 1 H); $^{13}$C NMR (500 MHz, MeOD) δ 143.89, 142.41, 131.68 (q, $J_{CCF}$=32.6 Hz), 123.81 (q, $J_{CF}$=271.6 Hz), 1121.17, 76.61, 71.56, 41.44, 36.24, 22.05; HRMS [ESI, MH$^+$] m/z calcd for $C_{20}H_{22}F_6NO$ 406.1606, found 406.1623.

EXAMPLE 75

1-(3,5-bis(trifluoromethyl)benzyloxy)-4-methylamino-2-methyl-2-phenylbutane. 4-(3,5-bis(trifluoromethyl)benzyloxy)-3-methyl-3-phenylbutanenitrile (46.2 mg, 0.115 mmol) was treated with neat borane-dimethylsulfide complex for 2 hour at room temperature until completion of reaction. The excess amount of borane was removed under nitrogen stream. The residue was quenched further with methanol and then heated at 80° C. for 1 hour to decompose the borane-amine complex. The resultant solution was concentrated and re-dissolved in $CH_2Cl_2$. It was washed with brine and dried with sodium sulfate. After concentration, the residue was mixed with $K_2CO_3$ (200 mg) and methyl chloroformate (21.8 mg, 0.23 mmol) in anhydrous $CH_2Cl_2$. After stirring overnight, it was worked up routinely and submitted for preparative HPLC. The obtained carbamate was treated with lithium aluminun hydride (0.168 mmol) in THF at 80° C. for 1 hour. Afterwards the reaction mixture was concentrated to dryness under nitrogen stream, re-dissolved in methanol, and purified by preparative HPLC and then silica flash chromatography (10% methanol in $CH_2Cl_2$) to give 8.5 mg of the desired product as a free base. $^1$H NMR (500 MHz, $CDCl_3$) δ ppm 1.42 (s, 3 H) 1.93 (m, 1 H) 2.09 (m, 1 H) 2.35 (s, 3 H) 2.37 (m, 1 H) 2.52 (m, 1 H) 3.54 (s, 2 H) 7.24 (m, 2 H) 7.34 (m, 4 H) 7.65 (s, 2 H) 7.76 (s, 1 H); $^{13}$C NMR (500 MHz, $CDCl_3$) δ 144.64, 141.36, 131.68(q, $J_{CCF}$=33.3 Hz), 128.45, 127.14, 126.65, 126.34, 123.39, (q, $J_{CF}$=272.5 Hz), 121.4 (m), 80.33, 71.89, 47.16, 41.67, 38.03, 35.70, 22.76.

EXAMPLE 76

1-(3,5-bis(trifluoromethyl)benzyloxy)-4-dimethylamino-2-methyl-2-phenylbutane, trifluoroacetic acid salt. 4-(3,5-bis(trifluoromethyl)benzyloxy)-3-methyl-3-phenylbutanenitrile 4-(3,5-bis(trifluoromethyl)benzyloxy)-3-methyl-3-phenylbutanenitrile (12 mg, 0.030 mmol) was dissolved in small amount of THF (100 ul) and neat borane-dimethylsulfide complex (1 ml) was added. The mixture was heated at 80° C. for 1.5 hours until completion of the reduction. Afterwards excess borane was removed under nitrogen stream, the residue was quenched with methanol and heated at 80° C. for 1 hour. 60% of the crude mixture was taken and concentrated to dryness. It was mixed with formaldehyde (16 mg, 37 wt % in water, 0.2 mmol) in methanol (1 ml) and sodium borohydride powder (11.4 mg, 0.3 mmol) was added. The reaction went complete instantly with release of heat. Afterwards it was filtered and diluted with methanol and purified by preparative HPLC to give 4.0 mg of the desired product as a trifluoroacetic acid salt. $^1$H NMR (500 MHz, MeOD) δ ppm 1.50 (s, 3 H) 2.16 (m, 1 H) 2.35 (m, 1 H) 2.86 (m, 7 H) 3.06 (m, 1 H) 3.66 (d, J=9.16 Hz, 1 H) 3.73 (d, J=9.16 Hz, 1 H) 4.68 (m, 2 H) 7.29 (t, J=7.17 Hz, 1 H) 7.39 (t, J=7.63 Hz, 2 H) 7.45 (m, 2 H) 7.85 (s, 1 H) 7.89 (s, 1 H); $^{13}$C NMR (500 MHz, MeOD) δ 140.70, 143.43, 132.80 (q, $J_{CCF}$=33.5 Hz), 129.78, 128.64, 127.98, 127.46, 124.87(q, $J_{CF}$=271.6 Hz), 122.24, 80.49, 72.68, 55.79, 43.48, 42.57, 34.22, 23.08; HRMS [ESI, MH$^+$] m/z calcd for $C_{22}H_{26}F_6NO$ 434.1919, found 434.1931.

EXAMPLE 77

1-(3,5-bis(trifluoromethyl)benzyloxy)-3-amino-2-methyl-2-phenylpropane, trifluoroacetic acid salt. 3-(3,5-bis(trifluoromethyl)benzyloxy)-2-methyl-2-phenylpropanal (75 mg, 0.192 mmol) and amine (0.48 ml, 2.0 M in methanol, 0.96 mmol) were mixed with acetic acid (58 mg, 0.96 mmol) in anhydrous THF (3 ml). The mixture was stirred for 10 minutes at room temperature before sodium triacetoxyborohydride (60.8 mg, 0.288) was added. The reaction mixture was stirred overnight and concentrated under nitrogen stream. The residue was dissolved in methanol, filtered and submitted for preparative HPLC. 6.9 mg of the desired product was obtained as a trifluoroacetic acid salt. $^1$H NMR (500 MHz, MeOD) δ ppm 1.51 (s, 3 H) 3.45 (m, 2 H) 3.70 (d, J=9.46 Hz, 1 H) 3.91 (d, J=9.16 Hz, 1 H) 4.74 (s, 2 H) 7.35 (t, J=6.71 Hz, 1 H) 7.44 (t, J=7.63 Hz, 2 H) 7.49 (m, 2 H) 7.91 (s, 3 H); $^{13}$C NMR (500 MHz, MeOD) δ 142.86, 142.09, 132.90 (q, JCCF=32.6 Hz), 130.18, 128.98, 128.78, 124.85 (q, $J_{CF}$=271.6 Hz), 122.48, 117.97 (TFA, q, $J_{CF}$=271.6 Hz), 78.69, 72.88, 48.14, 42.29, 21.90; HRMS [ESI, MH$^+$] m/z calcd for $C_{19}H_{20}F_6NO$ 392.1449, found 392.1465.

EXAMPLE 78

1-(3,5-bis(trifluoromethyl)benzyloxy)-3-methylamino-2-methyl-2-phenylpropane, trifluoroacetic acid salt. 3-(3,5-bis(trifluoromethyl)benzyloxy)-2-methyl-2-phenylpropanal (33 mg, 0.085 mmol) was mixed with excess amount of methylamine in methanol (2M, 1 ml, 2 mmol) and sodium borohydride (31 mg, 0.83 mmol) was added. After completion of the reaction, the reaction mixture was submitted for preparative HPLC and 15.6 mg of the desired product was obtained as a white trifluoroacetic acid salt. $^1$H NMR (500 MHz, MeOD) δ ppm 1.52 (s, 3 H) 2.70 (s, 3 H) 3.54 (s, 2 H) 3.70 (d, J=9.16 Hz, 1 H) 3.94 (d, J=9.46 Hz, 1 H) 4.75

(s, 2 H) 7.37 (m, 1 H) 7.45 (m, 2 H) 7.50 (m, 2 H) 7.93 (s, 3 H); $^{13}$C NMR (500 MHz, MeOD) δ 161.97 (TFA, q, JCCF=34.6 Hz), 141.73, 140.93, 131.80 (q, JCCF=33.6 Hz), 129.20, 128.09, 127.81, 126.46, 123.81 (q, $J_{CF}$=272.6 Hz), 121.49, 117.23 (TFA, q, $J_{CF}$=292.7 Hz), 77.62, 71.82, 57.47, 42.05, 34.38, 21.24; HRMS [ESI, MH$^+$] m/z calcd for $C_{20}H_{22}F_6NO$ 406.1606, found 406.1616.

EXAMPLE 79

1-(3,5-bis(trifluoromethyl)benzyloxy)-3-dimethylamino-2-methyl-2-phenylpropane, trifluoroacetic acid salt. 3-(3,5-bis(trifluoromethyl)benzyloxy)-2-methyl-2-phenylpropanal (75 mg, 0.192 mmol) and dimethylamine (0.171 ml, 5.6 M in ethanol, 0.96 mmol) were mixed with acetic acid (58 mg, 0.96 mmol) in anhydrous THF (3 ml). The mixture was stirred for 10 minutes at room temperature before sodium triacetoxyborohydride (60.8 mg, 0.288) was added. The reaction mixture was stirred overnight and concentrated under nitrogen stream. The residue was dissolved in methanol, filtered and submitted for preparative HPLC. 24.9 mg of the desired product was obtained as a trifluoroacetic acid salt. $^1$H NMR (500 MHz, MeOD) δ ppm 1.56 (s, 3 H) 2.67 (s, 3 H) 2.74 (s, 3 H) 3.75 (m, 2 H) 3.92 (d, J=9.46 Hz, 1 H) 4.77 (s, 2 H) 7.37 (t, J=7.32 Hz, 1 H) 7.45 (t, J=7.63 Hz, 3 H) 7.55 (m, 2 H) 7.93 (s, 1 H) 7.95 (s, 2 H); $^{13}$C NMR (500 MHz, MeOD) δ 160.98 (TFA, q, JCCF=37.4 Hz), 141.59, 141.34, 131.84 (q, JCCF=33.6 Hz), 129.17, 128.18, 127.91, 126.65, 123.8 (q, $J_{CF}$=271.6 Hz), 121.56, 116.71 (TFA, q, JCCF=289.8 Hz), 77.51, 71.89, 66.02, 45.72, 45.46, 42.24, 21.49; HRMS [ESI, MH$^+$] m/z calcd for $C_{21}H_{24}F_6NO$ 420.1762, found 420.1764.

EXAMPLE 80

1-(3,5-bis(trifluoromethyl)benzylthio)-4-amino-2-phenylbutane-2-ol. 4-(3,5-bis(trifluoromethyl)benzylthio)-3-hydroxy-3-phenylbutanenitrile (26 mg) was dissolved in neat borane dimethylsulfide complex (3 ml) and stirred at RT for 2 hours. The excess borane dimethylsulfide complex was removed under nitrogen stream and the residue was carefully quenched by slow addition of methanol and heated at 70° C. for a while. The methanol solution was then purified by preparative HPLC to give 10.2 mg of 1-(3,5-bis(trifluoromethyl)benzylthio)-4-amino-2-phenylbutane-2-ol TFA salt as a clean oil. $^1$H NMR (500 MHz, MeOD) δ ppm 7.84 (1 H, s) 7.81 (2 H, s) 7.49 (2 H, d, J=7.32 Hz) 7.42 (2 H, t, J=7.78 Hz) 7.34 (1 H, t, J=7.32 Hz) 3.64–3.71 (2 H, m) 3.02 (1 H, d, J=113.73 Hz) 2.95 (1 H, d, J=13.73 Hz) 2.84–2.91 (1 H, m) 2.73 (1 H, ddd, J=12.89, 7.86, 5.49 Hz) 2.30–2.37 (1 H, m) 2.25 (1 H, ddd, J=13.89, 8.39, 5.19 Hz). $^{13}$C NMR (126 MHz, MeOD) δ ppm 144.16 (s) 142.52 (s) 131.69 (q, JCCF=33.59 Hz) 129.49 (s) 128.59 (s) 127.60 (s) 125.67 (s) 123.79 (q, $J_{CF}$=271.60 Hz) 120.73–120.79 (m) 76.27 (s) 44.94 (s) 37.95 (s) 36.15 (s) 36.04 (s). MS [ESI, MH$^+$] m/z calcd for C19H20F6NOS 424.12, found 424.10.

EXAMPLE 81

1-(3,5-bis(trifluoromethyl)benzylamine-4-amino-2-phenylbutan-2-ol. N-(3,5-bis(trifluoromethyl)benzyl-3-cyano-2-hydroxy-2-phenylpropanamide (20 mg) was dissolved in neat borane dimethylsulfide complex (1.5 ml) and stirred at RT for 1 hour. The excess borane dimethylsulfide complex was removed under nitrogen stream and the residue was carefully quenched by slow addition of methanol. The methanol solution was heated to 70° C. for a while and was then purified by preparative HPLC to give 5.3 mg of 1-(3,5-bis(trifluoromethyl)benzylamine-4-amino-2-phenylbutan-2-ol TFA salt as clean oil. $^1$H NMR (500 MHz, MeOD) δ ppm 8.11 (3 H, s) 7.52–7.57 (2 H, m) 7.49 (2 H, t, J=7.63 Hz) 7.42 (1 H, t, J=7.17 Hz) 4.38 (1 H, d, J=13.73 Hz) 4.32 (1 H, d, J=13.43 Hz) 3.54 (1 H, d, J=12.82 Hz) 3.46 (1 H, d, J=12.82 Hz) 2.89–2.98 (1 H, m) 2.55 (1H, ddd, J=12.51, 10.53, 5.04 Hz) 2.23–2.32 (2 H, m). HRMS [ESI, MH$^+$] m/z calcd for C19H21F6N2O 407.1558, found 407.1568;

We claim:
1. A compound of Formula I

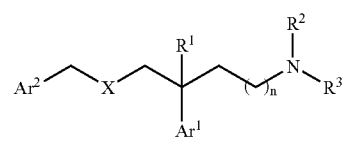

where:
Ar$^1$ is phenyl, naphthalenyl, or thienyl with 0–2 substituents selected from the group consisting of $C_{1-6}$alkyl, $C_{1-6}$alkoxy, trifluoromethyl, trifluoromethoxy, cyano, halo, and N(R$^4$)(R$^4$);
Ar$^2$ is phenyl substituted with 0–5 substituents selected from the group consisting of $C_{1-6}$alkyl, $C_{1-6}$alkoxy, trifluoromethyl, trifluoromethoxy, cyano, and halo;
R$^1$ is hydrogen, hydroxyl, $C_{1-6}$alkyl, or $C_{1-6}$alkoxy;
R$^2$ is hydrogen or $C_{1-6}$alkyl;
R$^3$ is hydrogen or $C_{1-6}$alkyl;
R$^4$ is hydrogen or $C_{1-6}$alkyl;
X is O, S, or NR$^4$; and
n is 1;
or a pharmaceutically acceptable salt or solvate thereof.
2. A compound of claim 1 where Ar$^1$ is phenyl substituted with 0–2 substituents selected from methyl, methoxy, or halo.
3. A compound of claim 1 where Ar$^1$ is naphthalenyl or thienyl.
4. A compound of claim 1 where Ar$^2$ is phenyl substituted with 0–2 substituents selected from the group consisting of $C_{1-6}$alkyl, $C_{1-6}$alkoxy, trifluoromethyl, trifluoromethoxy, cyano, and halo.
5. A compound of claim 4 where Ar$^2$ is substituted with 2 substituents selected from methyl, halo, and trifluoromethyl.
6. A compound of claim 1 where R$^1$ is hydrogen, methyl, or hydroxy.
7. A compound of claim 1 where R$^2$ and R$^3$ are independently hydrogen or methyl.
8. A compound of claim 1 where X is O.
9. A compound of claim 1 selected from group consisting of
1-(3,5-bis(trifluoromethyl)benzyloxy)-4-amino-2-phenylbutan-2-ol;
1-(3,5-bis(trifluoromethyl)benzyloxy)-4-(dimethylamino)-2-phenylbutan-2-ol;
1-(3,5-bis(trifluoromethyl)benzyloxy)-4-(methylamino)-2-phenylbutan-2-ol;
(R)-1-(3,5-bis(trifluoromethyl)benzyloxy)-4-amino-2-phenylbutan-2-ol;
(S)-1-(3,5-bis(trifluoromethyl)benzyloxy)-4-amino-2-phenylbutan-2-ol;
1-(3,5-bis(trifluoromethyl)benzyloxy)-4-amino-2-p-tolylbutan-2-ol;

1-(3,5-bis(trifluoromethyl)benzyloxy)-4-amino-2-(3,4-dichlorophenyl)butan-2-ol;
1-(3,5-bis(trifluoromethyl)benzyloxy)-4-amino-2-(naphthalen-2-yl)butan-2-ol;
1-(3,5-bis(trifluoromethyl)benzyloxy)-4-amino-2-(3-fluorophenyl)butan-2-ol;
1-(3,5-bis(trifluoromethyl)benzyloxy)-4-amino-2-(4-fluoro-3-methylphenyl)butan-2-ol;
1-(3,5-bis(trifluoromethyl)benzyloxy)-4-amino-2-(3-methoxyphenyl)butan-2-ol;
1-(3,5-bis(trifluoromethyl)benzyloxy)-4-amino-2-(3,4-difluorophenyl)butan-2-ol;
1-(3,5-bis(trifluoromethyl)benzyloxy)-4-amino-2-(4-(dimethylamino)phenyl)butan-2-ol;
1-(3,5-bis(trifluoromethyl)benzyloxy)-4-amino-2-m-tolylbutan-2-ol;
1-(3,5-bis(trifluoromethyl)benzyloxy)-4-amino-2-(3,5-dimethylphenyl)butan-2-ol;
1-(3,5-bis(trifluoromethyl)benzyloxy)-4-amino-2-(3,5-difluorophenyl)butan-2-ol;
1-(3,5-bis(trifluoromethyl)benzyloxy)-4-amino-2-(4-methoxyphenyl)butan-2-ol;
1-(3,5-bis(trifluoromethyl)benzyloxy)-4-amino-2-(3-chlorophenyl)butan-2-ol;
1-(3,5-bis(trifluoromethyl)benzyloxy)-4-amino-2-(4-methylnaphthalen-1-yl)butan-2-ol;
1-(3,5-bis(trifluoromethyl)benzyloxy)-4-amino-2-(3-fluoro-4-methoxyphenyl)butan-2-ol;
1-(3,5-bis(trifluoromethyl)benzyloxy)-4-amino-2-(3-chloro-5-fluorophenyl)butan-2-ol;
1-(3,5-bis(trifluoromethyl)benzyloxy)-4-amino-2-(5-fluoro-2-methoxyphenyl)butan-2-ol;
1-(3,5-bis(trifluoromethyl)benzyloxy)-4-amino-2-(2,3-dimethylphenyl)butan-2-ol;
1-(3,5-bis(trifluoromethyl)benzyloxy)-4-amino-2-(2,5-dimethoxyphenyl)butan-2-ol;
1-(3,5-bis(trifluoromethyl)benzyloxy)-4-amino-2-(4-methoxy-2-methylphenyl)butan-2-ol;
1-(3,5-bis(trifluoromethyl)benzyloxy)-4-amino-2-(5-fluoro-2-methylphenyl)butan-2-ol;
1-(3,5-bis(trifluoromethyl)benzyloxy)-4-amino-2-(2,4-dimethylphenyl)butan-2-ol;
1-(3,5-bis(trifluoromethyl)benzyloxy)-4-amino-2-(4-fluoro-2-methylphenyl)butan-2-ol;
1-(3,5-bis(trifluoromethyl)benzyloxy)-4-amino-2-(3,4-dimethylphenyl)butan-2-ol;
1-(3,5-bis(trifluoromethyl)benzyloxy)-4-amino-2-(3-fluoro-4-methylphenyl)butan-2-ol;
1-(3,5-bis(trifluoromethyl)benzyloxy)-4-amino-2-(naphthalen-1-yl)butan-2-ol;
1-(3,5-bis(trifluoromethyl)benzyloxy)-4-amino-2-(4-propylphenyl)butan-2-ol;
1-(3,5-bis(trifluoromethyl)benzyloxy)-4-amino-2-(3-fluoro-2-methylphenyl)butan-2-ol;
1-(3,5-bis(trifluoromethyl)benzyloxy)-4-amino-2-(2,5-dimethylphenyl)butan-2-ol;
1-(3,5-bis(trifluoromethyl)benzyloxy)-4-amino-2-(4-ethylphenyl)butan-2-ol;
1-(3,5-bis(trifluoromethyl)benzyloxy)-4-amino-2-(3,4-dimethoxyphenyl)butan-2-ol;
1-(3,5-bis(trifluoromethyl)benzyloxy)-4-amino-2-(4-chloro-2-methylphenyl)butan-2-ol;
1-(3,5-bis(trifluoromethyl)benzyloxy)-4-amino-2-(4-fluorophenyl)butan-2-ol;
1-(3,5-bis(trifluoromethyl)benzyloxy)-4-amino-2-(4-chlorophenyl)butan-2-ol;
1-(3,5-bis(trifluoromethyl)benzyloxy)-4-amino-2-o-tolylbutan-2-ol;
1-(3,5-bis(trifluoromethyl)benzyloxy)-4-amino-2-(thiophen-2-yl)butan-2-ol;
1-(3,5-bis(trifluoromethyl)benzyloxy)-4-amino-2-(2-methoxyphenyl)butan-2-ol;
1-(3,5-bis(trifluoromethyl)benzyloxy)-4-amino-2-(2,4-dimethoxyphenyl)butan-2-ol;
4-amino-1-(benzyloxy)-2-phenylbutan-2-ol;
1-(3-bromobenzyloxy)-4-amino-2-phenylbutan-2-ol;
1-(4-(trifluoromethoxy)benzyloxy)-4-amino-2-phenylbutan-2-ol;
1-(2-chlorobenzyloxy)-4-amino-2-phenylbutan-2-ol;
1-(3-fluoro-5-(trifluoromethyl)benzyloxy)-4-amino-2-phenylbutan-2-ol;
1-(2-bromobenzyloxy)-4-amino-2-phenylbutan-2-ol;
1-(3,5-dimethylbenzyloxy)-4-amino-2-phenylbutan-2-ol;
1-(2-(trifluoromethyl)benzyloxy)-4-amino-2-phenylbutan-2-ol;
1-(3-(trifluoromethyl)benzyloxy)-4-amino-2-phenylbutan-2-ol;
1-(4-(trifluoromethyl)benzyloxy)-4-amino-2-phenylbutan-2-ol;
1-(2-fluorobenzyloxy)-4-amino-2-phenylbutan-2-ol;
1-(3-fluorobenzyloxy)-4-amino-2-phenylbutan-2-ol;
1-(4-fluorobenzyloxy)-4-amino-2-phenylbutan-2-ol;
1-(3-methylbenzyloxy)-4-amino-2-phenylbutan-2-ol;
1-(3,5-dichlorobenzyloxy)-4-amino-2-phenylbutan-2-ol;
1-(2-methoxybenzyloxy)-4-amino-2-phenylbutan-2-ol;
1-(3-methoxybenzyloxy)-4-amino-2-phenylbutan-2-ol;
1-(3,5-difluorobenzyloxy)-4-amino-2-phenylbutan-2-ol;
1-(3-chlorobenzyloxy)-4-amino-2-phenylbutan-2-ol;
1-(4-bromobenzyloxy)-4-amino-2-phenylbutan-2-ol;
1-(2-methylbenzyloxy)-4-amino-2-phenylbutan-2-ol;
1-(3,5-dibromobenzyloxy)-4-amino-2-phenylbutan-2-ol;
1-(3-(trifluoromethoxy)benzyloxy)-4-amino-2-phenylbutan-2-ol;
1-(4-chlorobenzyloxy)-4-amino-2-phenylbutan-2-ol;
1-(3,5-bis(trifluoromethyl)benzyloxy)-4-amino-2-(phenyl)butane;
1-(3,5-bis(trifluoromethyl)benzyloxy)-4-(methylamino)-2-(phenyl)butane;
1-(3,5-bis(trifluoromethyl)benzyloxy)-4-(dimethylamino)-2-(phenyl)butane;
1-(3,5-bis(trifluoromethyl)benzyloxy)-4-amino-2-methyl-2-(phenyl)butane;
1-(3,5-bis(trifluoromethyl)benzyloxy)-4-(methylamino)-2-methyl-2-(phenyl)butane;
1-(3,5-bis(trifluoromethyl)benzyloxy)-4-(dimethylamino)-2-methyl-2-(phenyl)butane;
1-(3,5-bis(trifluoromethyl)benzylthio)-4-amino-2-phenylbutane-2-ol; and
1-(3,5-bis(trifluoromethyl)benzylamine-4-amino-2-phenylbutan-2-ol;
or a pharmaceutically acceptable salt or solvate thereof.

10. A composition comprising a pharmaceutically acceptable amount of a compound of claim 1 and at least one pharmaceutically acceptable carrier.

11. A method for treating a disorder associated with aberrant levels of tachykinins or serotonin comprising administering an effective amount of a compound of claim 1 to a patient afflicted with the disorder.

12. The method of claim 11 where the disorder is anxiety.

13. The method of claim 11 where the disorder is depression, obsessive compulsive disorder, bulimia, or panic disorder.

* * * * *